United States Patent
Almeida Regitano et al.

(10) Patent No.: US 10,626,459 B2
(45) Date of Patent: Apr. 21, 2020

(54) METHODS AND KITS FOR THE IDENTIFICATION OF ANIMALS HAVING A GREATER POTENTIAL FOR DESIRABLE CHARACTERISTICS, AND FOR THE EARLY IDENTIFICATION OF FAT DEPOSITS IN BOVINES

(75) Inventors: Luciana Correia de Almeida Regitano, Sao Carlos (BR); Gisele Batista Veneroni, Sao Carlos (BR); Polyana Cristine Tizioto, Sao Carlos (BR)

(73) Assignees: EMPRESA BRASILEIRA DE PESQUISA ACROPECUARIA—EMBRAPA, Plano Piloto Brasilia-DF (BR); FUNDACAO UNIVERSIDADE FEDERAL DE SAO CARLOS—UFSCar, Sao Carlos Sao Paulo, SP (BR); FUNDACAO DE AMPARO A PESQUISA DO ESTADO DE SAO PAULO-FAPESP, Lapa Sao Paulo (BR)

( * ) Notice: Subject to any disclaimer, the term of this patent is extended or adjusted under 35 U.S.C. 154(b) by 0 days.

(21) Appl. No.: 13/497,501

(22) PCT Filed: Sep. 15, 2010

(86) PCT No.: PCT/BR2010/000301
§ 371 (c)(1),
(2), (4) Date: Aug. 30, 2012

(87) PCT Pub. No.: WO2011/032243
PCT Pub. Date: Mar. 24, 2011

(65) Prior Publication Data
US 2013/0029328 A1    Jan. 31, 2013

(30) Foreign Application Priority Data

Sep. 15, 2009   (BR) .................................. 0903769

(51) Int. Cl.
*C12Q 1/68*      (2018.01)
*C12P 19/34*     (2006.01)
*C12Q 1/6876*    (2018.01)
*G01B 17/02*     (2006.01)

(52) U.S. Cl.
CPC ........... *C12Q 1/6876* (2013.01); *G01B 17/02* (2013.01); *C12Q 2600/124* (2013.01); *C12Q 2600/156* (2013.01)

(58) Field of Classification Search
CPC .................. G01B 17/02; C12Q 1/6876; C12Q 2600/124; C12Q 2600/156
See application file for complete search history.

(56) References Cited

PUBLICATIONS

ASAP1 ArfGAP with SH3 domain, ankyrin repeat and PH domain 1 [ *Bos taurus* (cattle) ] Gene ID: 327705 (Mar. 29, 2014) from https://www.ncbi.nlm.nih.gov/gene/327705, pp. 1-6.*
BD SpotLight Random Primer Labeling Kit User Manual (Aug. 22, 2003) Cat. No. 634801 or K1027-1 from BD Bioscience Clontech, pp. 1-11.*
DbSNP submitted SNP (SS) Details: ss141355216 (May 22, 2009), from http://www.ncbi.nlm.nih.gov/, pp. 1-2.*

* cited by examiner

*Primary Examiner* — Stephen T Kapushoc
(74) *Attorney, Agent, or Firm* — Sughrue Mion, PLLC

(57) ABSTRACT

The present invention relates to a method and a kit for the identification of animals having greater potential for desirable characteristics of meat quality, rib eye area (REA), weaning weight and 18-month weight by means of the analysis of specific markers.
The invention also refers to a method and a kit for the early identification of fat deposition in bovines.

3 Claims, 1 Drawing Sheet

Specification includes a Sequence Listing.

METHODS AND KITS FOR THE IDENTIFICATION OF ANIMALS HAVING A GREATER POTENTIAL FOR DESIRABLE CHARACTERISTICS, AND FOR THE EARLY IDENTIFICATION OF FAT DEPOSITS IN BOVINES

CROSS REFERENCE TO RELATED APPLICATIONS

This application is a National Stage of International Application No. PCT/BR2010/000301, filed on Sep. 15, 2010, which claims priority from Brazilian Patent Application No. PI 0903769-1 filed on Sep. 15, 2009, the contents of all of which are incorporated herein by reference in their entirety.

FIELD OF THE INVENTION

The present invention relates to a method for the identification of animals having greater potential for the deposition of subcutaneous fat by means of the analysis of specific molecular markers. The simple and correct identification provided the method may be very effective in genetic breeding of bovines.

STATE OF THE ART

Currently, Brazil has the world's second-largest cattle herd, second only to India (USDA. PRODUCTION, SUPPLY AND DISTRIBUTION ONLINE. Reports. Livestock. Cattle selected countries summary. Washington, D.C., 2009. Available at: <http://www.fas.usda.gov/psdonline/psdReport.aspx?hidReportRetrievalName=Cattle+Summary+Selected+Countries&hidReportRetrievalID=1648&hidReportRetrievalTemplateID=7>. Accessed in: January 2009).

Most of the cattle in Brazil are *Bos indicus* bovines, which are well adapted to the Brazilian environment, however, *Bos taurus* bovines also known as European Cattle provide better carcass quality.

Brazilian bovine herd is mainly comprised of Zebu cattle, the Nellore breed having greater expression. Considering the whole extent of the Brazilian territory, the Nellore breed stands out in the number of animals and is essential for cross-breeding with European breeds. Nellore cattle is of Indian origin and is well adapted to Brazil since the Brazilian climate conditions are similar to those found in India (RESTLE, J.; VAZ, F. N.; FEIJÓ, G. L. D.; BRONDANI, I. L.; ALVES FILHO, D. C.; BERNARDES, R. A. C.; FATURI, C.; PACHECO, P. S. Características de Carcaça de Bovinos de Corte Inteiros ou Castrados de Diferentes Composições Raciais Charolês X Nelore. Rev. Bras. Zootec., v.29, n.5, pp. 1371-1379, 2000).

Although Zebu breeds are included in breeding programs and are selected mainly for growth, reproductive and morphological characteristics, they have been less intensively selected due to some attributes of economic value, such as meat quality, especially concerning tenderness of the muscle fibers.

The meat product is the ultimate goal of every beef cattle breeding program and also of activities related to the slaughter and commercialization of these animals. Due to the large number of breeds and crossbreeds generated by cattle for slaughter, there is a wide variation in the carcasses, which have to be classified in order to meet the demands of different consumer markets (Bonfim, L. M. Caracteristicas Qualitativas das Carcaças: Tipificação de Carcaça e Área de Olho de Lombo. Available at http://www.rehagro.com.br/siterehagro/publicacao.do?cdnoticia=505>2003).

Beef carcass value is determined by many factors such as weight, fat cover (subcutaneous fat) and intramuscular fat or marbling (PEROTTO, D.; MOLETTA, J. L.; CUBAS, A. C. Características da carcaça de bovinos canchim e Aberdeen angus e de seus cruzamentos recíprocos terminados em confinamento. Ciência Rural, Santa Maria, v. 29, n. 2, pp. 331-338, 1999). Meat packing industry has avoided carcasses having fat thickness lower than 3 mm and higher than 6 mm, since in products with fat cover of less than 3 mm there is a darkening of the outer part of muscles caused by the cold inside the cold storage chambers and shortening of the muscle fibers caused by the faster cooling speed, which has a negative impact on meat tenderness. Fat is also an important component in beef flavor.

Several linear measurements have been made in the carcass or the surface of meat cuts in order to identify which can serve as reliable composition indicators. Muscle development can be better estimated through the observation of the transverse area of *Longissimus dorsi* muscle at the last rib, which is referred to as rib eye area (REA). As a consequence, the *Longissimus dorsi* muscle area has been more used by researchers, the meat industry and breed associations as an indicator of muscularity than any other measurement. The establishment of relationships between REA and the cold carcass weight has also been attempted. Rib eye area measurement as a function of the cold carcass weight (REA/100 kg cold carcass) enables a better interpretation of the information related to the rib eye area hence facilitating the identification of animals superior in muscularity (Bonfim, L. M. Características Qualitativas das Carcaças: Tipificação de Carcaça e Área de Olho de Lombo. Available at http://www.rehagro.com.br/siterehagro/publicacao.do?cdnoticia=505>2003).

National and international markets have required higher quality products that meet pre-established standards. Thus, low cost preparation of high quality products has been desired by cattle breeders and the meat packing industry. Animal breeding is of great importance in this context. Traditional animal breeding programs promote fundamental progress in productive and reproductive performance of cattle, but they have limitations when it comes to selecting traits that are difficult to measure or that are detected later and low heritability traits. In this regard, molecular markers may help genetic animal breeding.

Accuracy of traditional selection methods may be increased by implementing marker-assisted selection (MAS) using molecular markers for detecting genetically superior individuals. Implementation of MAS in breeding programs provides greater benefits when the selected trait is of low heritability, is difficult and/or expensive to measure or can only be measured at an advanced age, such as traits related to resistance to diseases, meat quality (tenderness, fat deposition and the like), fertility, productive efficiency and milk production traits (BRITO, F. V.; CARDOSO, V.; CARVALHEIRO, R. et al. A biotecnologia no melhoramento genético animal. Dec. 26, 2006, available at: http://www.beefpoint.com.br/?noticiaID=33237&actA=7&areaID=60&secaoID=170>) and also traits such as maternal ability, carcass yield, fertility and sex-limited traits (EENENNAAM, A. V. Marker-Assisted Selection in Beef Cattle. Available at: http://animalscience.ucdavis.edu/animalbiotech/Outreach/Marker Assisted Selection in Beef Cattle.pdf>2004).

Analyses of the bovine genome, including quantitative trait locus (QTLs) mapping, single-nucleotide polymorphism (SNPs) and more recently large-scale genotyping, may contribute for early detection of cattle. Thus, molecular markers are intended to be used to increase the selection efficiency, to anticipate the time of selection, or to improve selection accuracy (DAVIS, G. P; DANISE S. K. The Impact of Genetic Markers on Selection. J. Anim. Sci. v. 76, pp. 2331-2339, 1998).

One of the most studied markers is SNP (single-nucleotide polymorphism) which consists of changing a single base in the DNA sequence with the possibility of two nucleotide types at a given position. The origin of the SNPs is based on individual variations arising from point mutations (nucleotide substitutions, additions or deletions).

A SNP may be detected by DNA sequencing. Dideoxy or chain-termination sequencing is based on the incorporation of deoxynucleotides (dNTPs) and dideoxynucleotides (ddNTPs) to a DNA strain being formed using the DNA of interest as a template. Once the ddNTPs are added to the chain, extension thereof is discontinued as ddNTPs lack a 3' hydroxyl group (OH) that is necessary for the next deoxynucleotide (dNTP) to bind. These ddNTPs are labeled and can be detected, thereby identifying the nucleotide sequence. After several cycles, DNA strands of many different lengths are obtained, all ending with different ddNTPs that are further indentified in an automated sequencer (REGITANO, L. C. A., et al. Protocolos de Biologia Molecular Aplicada à Produção Animal. 1. ed. online. Embrapa Pecuária Sudeste, 2007).

Many works using molecular markers have been made to study economically important traits. Moore et al. (MOORE, S. S.; LI, C.; BASARAB, J. et al. Fine mapping of quantitative trait loci and assessment of positional candidate genes for backfat on bovine chromosome 14 in a commercial line of Bos taurus. Journal of Animal Science, v. 81, pp. 1919-1925, 2003.) and Casas et al., (CASAS, E.; SHACKELFORD, S. D.; KEELE, J. W. et al. Quantitative trait loci affecting growth and carcass composition of cattle segregating alternate forms of myostatin. Journal of Animal Science, v. 78, pp. 560-569, 2000) described a QTL (Quantitative Trait Loci) for fat thickness in the centromeric region of BTA14. The thyroglobulin gene was then mapped in this region and it has been indicated as a candidate gene for fat deposition traits in beef cattle.

Many studies using molecular markers, such as Ge et al., 2001 (GE, W.; DAVIS, M. E.; HINES, H. C.; IRVIN, K. M.; SIMMEN, R. C. Association of a genetic marker with blood serum insulin-like growth factor-I concentration and growth traits in Angus cattle. J. Anim Sci., v. 79, pp. 1757-1762, 2001); Cho et al., 2008 (CHO, S.; PARK, T. S.; CHEONG, H. S.; NAMGOONG. S.; PARK, B. L.; LEE, H. W.; HAN, C. S.; CHEONG, I. C.; KIM, H.; SHIN, H. D. Identification of genetic polymorphisms in FABP3 and FABP4 and putative association with back fat thickness in Korean native cattle. BMB Rep. v. 41, n. 1, pp. 29-34, 2008) and Guo et al., 2008 (GUO, H.; LIU, W. S.; TAKASUGA, A.; EYER, K.; LANDRITO, E.; XU, S. Z.; GAO, X.; REN, H. Y.; Mapping Expression, and Association Study of the bovine PSMC1 Gene. Springer Science, v. 46, pp. 347-355, 2008) have been made to study economically important traits.

Moore et al., described a QTL for fat thickness in the centromeric region of BTA14. The thyroglobulin gene was then mapped in this region and it has been indicated as a candidate gene for fat deposition traits in beef cattle. (S. S. Moore, C. Li, J. Basarab, W. M. Snelling, J. Kneeland, B. Murdoch, C. Hansen and B. Benkel) Fine mapping of quantitative trait loci and assessment of positional candidate genes for backfat on bovine chromosome 14 in a commercial line of Bos taurus. Journal of Animal Science, v. 81, pp. 1919-1925, 2003 and (E. Casas, S. D. Shackelford, J. W. Keele, R. T. Stone, S. M. Kappes and M. Koohmaraie) Quantitative trait loci affecting growth and carcass composition of cattle segregating alternate forms of myostatin. Journal of Animal Science, v. 78, pp. 560-569, 2000).

Barendse et al. (BARENDSE, W.; BUNCH, R.; THOMAS, M. et al. The TG5 DNa marker test formarbling capacity in Australian feedlot cattle. Available at: www.Beef.crc.org.au/Publications/Marblingsym/Day1/Tg5DNA>. Accessed in: March 2006, 2001) and Wood et al. (WOOD, I. A.; MOSER, G.; BURRELL, D. L.; MENGERSEN, K. L. & HETZEL, D. J.S. A meta-analytic assessment of a Thyroglobulin marker for marbling in beef cattle. Genetics Selection Evolution, v. 38, pp. 479-494, 2006) have found an association between a polymorphism in the 5' leader sequence of thyroglobulin gene with marbling and this polymorphism is the basis of GeneStar Marbling™ (Genetic Solution) commercial test. However, Casas et al., (CASAS, E.; WHITE, S. N.; RILEY, D. G. et al. Assessment of single nucleotide polymorphisms in genes residing on chromosomes 14 and 29 for association with carcass composition traits in Bos indicus cattle. Journal of animal Science, v. 83, pp. 13-19, 2005) have found an association between the same polymorphism and fat thickness, but not marbling, as well as Rincker et al. (RINCKER, C. B.; PYATT, N.A.; BERGER, L.L. et al. Relationship among GeneSTAR marbling marker, intramuscular fat deposition, and expected progeny differences in early weaned Simental steers. Journal of Animal Science, v. 84, pp. 686-692, 2006) who found no association between Tg5 and intramuscular fat.

In 2007, a study was carried out for the association of fat thickness of composite animals (Canchim-5/8 Charoles and 3/8 Zebu) with Tg5 and no significant results were obtained (Veneroni, 2007). Associação da região centromérica do cromossomo 14 com espessura de gordura em bovinos da raça Canchim. São Carlos, 2007. Masters dissertation—Center of Biological Sciences and Health—Federal University of São Carlos). The same study also tested the association with CSSM066 microsatellite (located at 2.95 Mb on BTA14, flanking the thyroglobulin gene) and it was significant for the trait in question.

These results corroborate the findings of Moore et al. (2003) (S. S. Moore, C. Li, J. Basarab, W. M. Snelling, J. Kneeland, B. Murdoch, C. Hansen and B. Benkel) Fine mapping of quantitative trait loci and assessment of positional candidate genes for backfat on bovine chromosome 14 in a commercial line of Bos taurus. Journal of Animal Science, v. 81, pp. 1919-1925, 2003, who also found no association of Tg5 with the expected breeding value (EBV) for fat thickness, but with the CSSM066 locus.

Therefore, although there are studies available indicating the existence of a QTL for fat thickness in the centromeric region of BTA14, the information is not conclusive, since some studies found no association between the possible candidate gene, thyroglobulin, and the trait in question.

Annotation of the bovine genome (Build 4.0—based on Btau_4.0, available at the NCBI database (National Center for Biotechnology Information) (www.ncbi.nlm.nih.gov)) has shown other genes involved in lipid metabolism and adipocyte differentiation, which genes are located in the QTL region for fat thickness in the centromeric region of BTA14, such as development and differentiation-enhancing factor 1 (DDEF1) gene that could be tested for an association with fat thickness and other traits of meat production.

Wood et al. 2006 (WOOD, I. A.; MOSER, G.; BURRELL, D. L.; MENGERSEN, K. L. & HETZEL, D. J.S. A meta-analytic assessment of a Thyroglobulin marker for marbling in beef cattle. Genetics Selection Evolution, v. 38, pp. 479-494, 2006) have found an association between a polymorphism in the 5' leader sequence of thyroglobulin gene with marbling and this polymorphism is the basis of GeneStar Marbling™ (Genetic Solution) commercial test. However, several authors found no association between Tg5 and intramuscular fat, but they did show that it was associated with the CSSM066 locus (located at 2.95 Mb on BTA14, flanking the thyroglobulin gene).

DDEF1 gene (Development and Differentiation-Enhancing Factor 1) is located at 9.7 Mb on BTA14, has 31 exons and a transcript of 5,330 base pairs (BIRNEY, E.; ANDREWS, D.; CACCAMO, M. et al. Ensembl 2006. Nucleic Acids Research January 1; 34. Database issue: D556-D561. 2009). DDEF1, also known as Arf-GAP, is a GTPase-activating protein (Arf-GAP domain) that ribosylates ADP. It interacts with signal transduction proteins involved in cellular growth and differentiation (such as SRK, FAK, Phosphatidylinositol-4,5-biphosphate and CRK) and also regulates remodeling of the actin cytoskeleton that is required for cellular motility (LIU, Y.; LOIJENS, J.C.; MARTIN, K.H. et al. The association of ASAP1, an ADP ribosylation factor-GTPase activating protein, with focal adhesion 18 kinase contributes to the process of focal adhesion assembly. Mol. Biol. Cell. v.13. pp. 2147-56, 2002).

Studies carried out with DDEF1 gene indicate that the product of this gene is an important signal transduction protein involved in adipogenesis (Frederick J. King, Erding Hu, David F. Harris, Pasha Sarraf, Bruce M. Spiegelman, and Thomas M. Roberts) DEF-1, a novel Src SH3 binding protein that promotes adipogenesis in fibroblastic cell lines. Mol Cell. Biol. v.19. pp. 2330-7, 1999). DDEF1 gene is located in BTA 14 and is a candidate gene for meat production traits. Veneroni et al. 2008 (VENERONI, G.B, MEIRELLES, S.L, GOUVEIA, J.J.S., SANTIAGO, A.C., OLIVEIRA, H.N., ALENCAR, M.M., REGITANO, L.C.A. Identificação de SNPs no gene DDEF1 bovino. In: 54° Congresso Brasileiro de Genética. Annals . . . Salvador, pp. 231, 2008.) have identified a SNP in intron 13 of the DDEF1 gene and investigated the possible association thereof with fat thickness in Canchim breed cattle.

There are documents in the state of the art that disclose the use of molecular markers associated with meat traits. However, to date, no information has been provided correlating the DDEF1 gene molecular marker, that is the object of the present invention, with the characteristics of meat quality, rib eye area (REA), weaning weight, 18-month weight and meat tenderness.

Document CN101624598 discloses two primers for calpain 1 (CAPN1) gene sequence having 520 bp. These primers may be used as a molecular marker in marker-assisted selection of cattle. CAPN1 gene is associated with *Longissimus* muscle tenderness in cattle. The present document correlates a marker with a trait (meat tenderness); the present invention describes a marker that is different from that disclosed by document CN101624598 and is correlated with other production traits (rib eye area, weaning weight and 18-month weight).

Document US2002142315 seeks protection for a method of obtaining beef cattle comprising a genetic predisposition for increased or decreased carcass or weaning weight. The method comprises the steps of: (a) assaying genetic material from at least one animal for a genetic polymorphism genetically linked to promoter P1 of exon 1A of the bovine growth hormone receptor gene, wherein said polymorphism is associated with increased or decreased carcass or weaning weight; and selecting a head of beef cattle comprising said polymorphism. Weaning weight is a quantitative trait. Quantitative traits are influenced by many genes in several loci, in the present invention, a specific gene (DDEF1) was associated, which is different from the gene disclosed in document US2002142315. DDEF1 gene has never been associated with production traits and it contributes to the total phenotypic variance of the characteristic of weaning weight.

Document US2007224623 refers to a method for identifying an animal having desirable beef marbling and/or subcutaneous fat, as compared to the general population of animals of that species. The method comprises determining the presence of one or more single nucleotide polymorphisms (SNP) in a DOPEY2 and/or KIAA1462 gene of the animal, wherein the single nucleotide polymorphism is indicative of beef marbling, subcutaneous fat, or a combination thereof. Production traits, such as fat deposition, are quantitative traits and are influenced by many genes. DDEF1 gene has never been associated with production traits, therefore, we have identified a new gene that contributes to the total phenotypic variance of some production traits.

Document WO2009059417 refers to a method for identifying an animal having desirable traits of: carcass quality, growth and/or feed efficiency, as compared to the general population of animals of that species, comprising determining the presence of one or more single nucleotide polymorphisms (SNP) in a CBFA2T1 and/or DECRI gene of the animal, wherein the single nucleotide polymorphism is indicative of carcass quality, growth and/or feed efficiency. In the present invention we have identified a new gene that is associated with production traits and described this association for *Bos indicus* (Nellore breed) animals that are the most important in the Brazilian beef cattle industry.

Document PI0501474-3 relates to a genetic test and the molecular markers thereof (oligonucleotide primers or primers) for use in the amplification of the 361 base pair-fragment containing C313Y and E291X mutations in the third exon of cattle myostatin gene, for use in marker-assisted selection in Piemontese and Marchigiana breeds of beef cattle. Potential users of this test are molecular biology laboratories, cattle farms for genotyping the offspring and for use in breeding and selection programs, meatpacking companies and butcher shops for improving meat yield and tenderness.

Document JP2001008688 discloses the preparation of a novel mismatch primer containing a specific base sequence and that is capable of exactly and rapidly detecting the mutant of PPARγ gene that is an important factor for judging the carnosity of beef and a master key for crossing bovine fat.

Patent application KR20040108418 seeks protection for a method for selecting beef cattle showing high fat accumulation in muscle, thereby selecting high quality of beef cattle with confidence, reproduction and rapidity without killing cattle.

Document U.S. Pat. No. 6,569,629 discloses a method of identifying a bovine animal or carcass having a genetic marker for marbled or tender beef, comprising: (a) extracting DNA from cells in a sample obtained from the animal or carcass; (b) assaying said DNA sample for detecting a fragment comprising a sequence which is identical to or fully complementary to the whole or part of SEQ ID NO. 1, wherein the presence of this DNA fragment indicates that the animal or carcass has a genetic marker for marbling. In another aspect, the genetic marker is a marker for tenderness and comprises the sequences of the group consisting of SEQ ID NO. 2, SEQ ID NO. 3, SEQ ID NO. 4 or combinations thereof. The compositions include primers which amplify markers for marbled or tender beef present in cattle or carcass genome and hybridize to probes for detecting markers for marbling or tenderness.

Document WO9803677 refers to a genetic marker used to distinguish amongst animals a trait for milk producing capabilities or muscular beef producing capabilities said genetic marker comprising a mutation in a fragment of a Pit-1 gene wherein after digestion with a restriction endonuclease three patterns of alleles are observed in which one of said allele patterns is fully mutated, being indicative of a trait of muscularity in said animal, while the two other allelic patterns, one being mutated and non-mutated, while the other being non-mutated and non-mutated, being indicative of a milk producing trait in said animal.

Document WO9923248 relates to a method of assessing the fat metabolism characteristics of an animal, comprising the step of testing the animal for the presence or absence of one or more markers selected from the group consisting of: a) an allele of the 5' untranslated region of the gene encoding thyroglobulin; b) an allele of the DNA polymorphism CSSM34, associated with the gene encoding retinoic acid receptor gamma (RARG); c) an allele of the DNA polymorphism ETH10, associated with 11-cis, 9-cis retinol dehydrogenase (RDH5).

Document WO2007012119 discloses a method for assessing a trait in a bovine animal selected from containing the traits: *Longissimus dorsi* peak force, intramuscular fat, retail beef yield and net feed intake and/or its component traits, comprising the steps of: (1) providing a nucleic acid from the bovine animal or carcass; (2) assaying for the occurrence of a single nucleotide polymorphism (SNP) identified (a) in any one of SEQ ID Nos: 1 to 1635, wherein the identification of said nucleotide occurrence as set forth in any one of SEQ ID NOs: 1171 to 1631 is associated with variation in *Longissimus dorsi* peak force, (b) in any of SEQ ID Nos: 214 to 842 is associated with intramuscular fat deposition, (c) in any one of SEQ ID NOs: 843 to 1170 is associated with retail beef yield and (d) in any one of SEQ ID NOs: 213 to 1632 is associated with net feed intake and/or its component traits.

Document US2009092978 seeks protection to a method for identifying an animal having desirable beef marbling score (BMS), subcutaneous fat depth (SFD), estimated stearoyl-CoA desaturase activities designated as R1=(14:1/14:0)×100%, R2=(16:1/16:0)×100% and R3=(18:1/18:0)×100%, relative amounts of saturated (SFA), monounsaturated (MUFA) and polyunsaturated fatty acids (PUFA), conjugated linoleic acid mg/100 g dry muscle (CLA), cholesterol mg/100 g dry muscle (CHOL), ribeye area (REA) or percent kidney, pelvic and heart fat (KPH) or any combination thereof, as compared to the general population of animals of that species, comprising determining the presence of single nucleotide polymorphisms in an UQCRC1 gene, wherein the single nucleotide polymorphisms are indicative of desirable beef marbling score (BMS), subcutaneous fat depth (SFD), estimated stearoyl-CoA desaturase activities designated as R1=(14:1/14:0)×100%, R2=(16:1/16:0)×100% and R3=(18:1/18:0)×100%, relative amounts of saturated (SFA), monounsaturated (MUFA) and polyunsaturated fatty acids (PUFA), conjugated linoleic acid mg/100 g dry muscle (CLA), cholesterol mg/100 g dry muscle (CHOL), ribeye area (REA) or percent kidney, pelvic and heart fat (KPH) or any combination thereof.

Document U.S. Pat. No. 7,303,878 discloses a method for evaluating porcine animals based on MC4R gene-related markers, which are indicated for the selection of animals having superior traits, such as marbling, pH and meat color. The method is based on a PCR reaction, the markers being identified by several knwon analysis techniques, particularly RFLPs.

Document U.S. Pat. No. 7,468,268 discloses methods and systems for the inference of cattle traits. Said methods, systems and compositions enable the identification and selection of superior animals by means of the genetic diversity observed in cattle, to improve quality and uniformity of meat production. The methods use genetic information and variants thereof, particularly SNPs markers, that are associated with traits such as those present at position 300 of the sequence designated Seq. ID 21645 and that enable the identification of information on marbling, tenderness, fat thickness, red meat production or average daily body weight gain. Sequence SEQ ID 21645 has similarity with sequences present on BTA4: ref|NW_001494915.2| Bt4_WGA463_4 and ref|NW_001494911.2|Bt4_WGA462_4. Therefore, the sequences of such patent are present in chromosome 4 and not 14.

DDEF1 protein localizes to newly forming focal complexes at the cell periphery and regulates cyclical changes in the cytoskeleton and focal adhesions (Randazzo P A, Andrade J, Miura K, et al. The Arf GTPase-activating protein ASAP1 regulates the actin cytoskeleton. Proc Natl Acad Sci USA 2000; 97:4011-6. Overexpression of DDEF1 protein interrupts focal readhesion, thereby blocking expansion and promoting cell motility (Furman C, Short S M, Subramanian RR, Zetter BR, Roberts TM. DEF-1/ASAP1 is a GTPase-activating protein (GAP) for ARF1 that enhances cell motility through a GAP-dependent mechanism. J Biol Chem 2002; 277:7962-9). The relationship between DDEF1 and adipogenesis has been demonstrated by King et al. (King, F.J.; Hu, E.; Harris, D.F. et al. DEF-1, a novel Src SH3 binding protein that promotes adipogenesis in fibroblastic cell lines. Cellular and molecular biology. v.19. pp. 2330-7, 1999) who purified and cloned DDEF1 protein from bovine brain cells and noted on cell culture that the expression of this protein caused differentiation of fibroblasts into adipocytes. This observation shows the role of the gene in adipocyte differentiation, making it a candidate gene for affecting the changes in fat thickness. Nevertheless, it does not necessarily entail a direct relationship of changes in the gene sequence with changes in fat thickness.

Fat deposition adds value and quality to the product and is increasingly demanded by consumers. This measurement is usually made by means of ultrasound procedures, but it should be performed in animals of up 18 months of age, since after that the vertebral transverse processes become more pronounced, making it impossible to fit correctly the ultrasound probe for a more accurate measurement.

Therefore, the possibility of predicting or determining this trait in an early and accurate manner may greatly increase the efficiency of breeding programs and may increase the value of reproductive animals (bulls and breeding cows) that are known to have this trait.

SUMMARY OF THE INVENTION

The present invention relates to the identification of molecular markers that are highly correlated with subcutaneous fat deposition.

A first embodiment of the invention relates to a method for the early and precise identification of subcutaneous fat deposition in bovines, comprising the steps of: (i) extracting DNA from the animals having potential for increased subcutaneous fat deposition; (ii) genotyping the DDEF1 gene; (iii) identifying in the genomic sequence as set forth in (ii) the genotype or genotypes or the genetic variant associated with higher and lower fat deposition, and (iv) establishing an association between the genotype and the phenotype, taking into account the allelic frequencies of the population being studied. Preferably, in step (ii) primers corresponding to SEQ ID No. 1, SEQ ID No. 2, SEQ ID No. 3 and SEQ. ID no. 4 are used.

```
SEQ ID No. 1:
ATATGGGAATCCTAGAGAGGAGACGTAAC

SEQ ID No. 2:
GGGAATCCTAGAGAGGAGACGTAAT

SEQ ID No. 3:
(Left): GACTAGAAATAGGAGACCCGGACC

SEQ ID No. 4:
(Right): GCCTTCCTCAAACCACACAT
```

The identification of the genotype or genotypes or the genetic variant of step (iii) may be carried out by means of known SNP analysis procedures, such as PCR-RFLP, mass spectrometry, sequencing, High Resolution Melting, allele-specific probes (TaqMan) and amplification with allele-specific primers (ARMS-PCR).

A second embodiment of the invention relates to a kit for the identification of animals having a greater potential for fat deposition, which comprises two primers external to the polymorphism, one internal allele-specific primer, reagents used in the PCR reaction. Alternatively, two specific restriction endonuclease- or fluorescence-labeled allele-specific probes for each SNP allele and a manual containing instructions for the identification of the results may be used.

The present invention further relates to a method for the identification of animals having greater potential for meat quality traits by means of the analysis of specific molecular markers. Particularly, the present technology is concerned with DDEF1 gene polymorphisms and the association thereof with the rib eye area (REA), weaning weight and 18-month weight in bovines.

In one embodiment, the invention refers to the isolated nucleic acid molecules characterized by being sequences selected from the group consisting of SEQ ID No. 1, SEQ ID No. 2, SEQ ID No. 3 or SEQ ID No. 4.

In a second embodiment of this method, the invention relates to a method for the early and precise identification meat production traits in bovines, comprising the steps of: (i) extracting DNA from the animals having potential for desirable characteristics of meat production; (ii) genotyping the DDEF1 gene; (iii) identifying in the genomic sequence as set forth in (ii) the genotype or genotypes or the genetic variant associated with rib eye area (REA), weaning weight and 18-month weight, and (iv) establishing an association between the genotype and the phenotype, taking into account the allelic frequencies of the population being studied.

In the third embodiment of the method, the invention relates to the use of a specific molecular marker selected from the group consisting of SEQ ID No. 1, SEQ ID No. 2, SEQ ID No. 3 or SEQ ID No. 4 in the recognition of the single base polymorphism (SNP) located in intron 13 of DDEF1 gene, that is associated with the following traits: rib eye area (REA), weaning weight and 18-month weight in bovines.

In the fourth embodiment of the method, the invention relates to a kit for the identification of animals having greater potential for meat quality traits, characterized by comprising two primers external to the polymorphism, one internal allele-specific primer, reagents used in the PCR reaction and, alternatively, two specific restriction endonuclease- or fluorescence-labeled allele-specific probes for each SNP allele, and a manual containing instructions for the identification of the results.

DETAILED DESCRIPTION OF THE INVENTION

Figure 1:
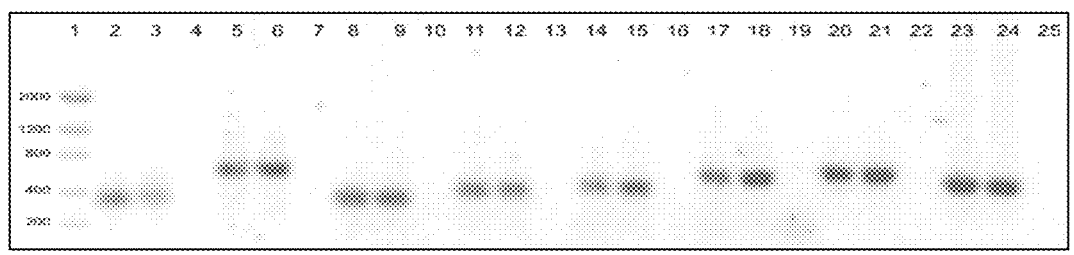
FIG. 1. 1% agarose gel for viewing the amplified fragments. Lane 1 corresponds to the low-mass DNA molecular weight ladder and lanes 2 to 25 correspond, respectively, to amplicons generated with RP2, RP2, RP2 negative, R2AG, R2AG, R2AG negative, R3A, R3A, R3A negative, R2S, R2S, R2S negative, R1A, R1A, R1A negative, RP1, RP1, RP1 negative, R1S, R1S, R1S negative, R2A, R2A and R2A negative primers.

The present invention relates to a method for the identification of animals having a greater potential for the deposition of subcutaneous fat by means of the analysis of specific molecular markers.

Experimental identification of a significant association between genotypes of the centromeric region of BTA 14 and subcutaneous fat thickness was used.

The method proposed herein comprises the following steps:

1—DNA samples were extracted from blood or semen of the animals. The extraction can be made according to procedures described by REGITANO (REGITANO, L. C. A. Introdução ao use de marcadores moleculares In: Regitano L. C. A. And Coutinho LL (Eds.) Biologic molecular aplicada à produção animal. Brasília: Embrapa Informação Tecnológica, 2001) or any procedure that enables access to the DNA within the cell nucleus.

2—Genotyping for the SNP in DDEF1 gene, which can be performed by PCR-ARMS preferably employing the primers listed in table 1:

TABLE 1

Primers designed for SNP genotyping in DDEF1 gene

| Primer | Gene | Sequence | Amplicon (bp) | SEQ ID NO: |
|---|---|---|---|---|
| DDEF1 In R allele G | DDEF1 | ATATGGGAATCCTAGAGAGGAGACGTAAC | 234 | 1 |
| DDEF1 In R allele A | DDEF1 | GGGAATCCAGAGAGGAGACGTAAT | 230 | 2 |
| DDEF1 Outer F | DDEF1 | GACTAGAAATAGGAGACCCGGACC | | 3 |
| DDEF1 outer R | DDEF1 | GCCTTCCTCAAACCACACAT | 570 | 4 |

PCR products are preferably analyzed (genotyping) in an ABI 3100 Avant sequencer (Applied Biosystems). Genotypes may be determined using GeneScan (version 3.7.1) and Genotyper (version 3.7) softwares. Genotyping may also be performed by any SNP analysis method, such as PCR-RFLP, mass spectrometry, sequencing, High Resolution Melting, or using allele-specific probes (TaqMan).

3—Identification of the genotype or genotypes, or the genetic variant associated with higher or lower fat deposition.

4—Use of suitable statistical methods to evaluate the results.

Genotype x phenotype association may vary depending on the breed/population being studied, i.e., the same genotype may be positively associated in one population, but negatively associated in another. Therefore, determination of which genotype must be selected is only possible after the appropriate statistical method is employed taking into account allele frequencies of the population being studied and the data distribution of a sample of the population where the diagnostic method is intended to be used. Such analysis may be performed using an animal model under the method of restricted maximum likelihood.

The invention is also embodied in the form of a kit for the identification of animals having a greater tendency for fat deposition, which comprises the four selected primers, flasks containing ordinary reagents to be used in the genotyping reaction in the proper concentrations (Tris-HCl, KCl, DMSO, MgCl2, dNTP, Taq DNA polymerase) and a manual containing instructions for the identification and interpretation of the results.

Known conditions and reagents are used in the DNA extraction step. For example, the extraction can be performed according to the procedures described by Regitano (2001) which, in short, consist of obtaining leucocytes by treating whole blood with a solution that promotes lysis of red cells; disrupting the leukocytes thus obtained in the presence of a detergent such as SDS and a proteolytic enzyme such as Proteinase K; removing the proteins from the solution by precipitation in the presence of a high concentration of ions such as $Na^+Cl^-$; precipitating the DNA in the presence of an alcohol such as ethanol or isopropanol and solubilizing it in an aqueous solution, preferably, Tris-EDTA buffer.

Proteins may be alternatively excluded from the solution by organic solvents, such as phenol in the presence or not of chloroform and isoamyl alcohol. It is also possible to use filtration through a cellulose column followed by elution of DNA that has adhered thereto.

The SNPs sequences are amplified using the PCR technique. In short, the reaction uses 20 to 200 ng of genomic DNA; 0.1 to 0.3 mM dNTPs; 1 to 2.0 mM $MgCl_2$; 20 mM TRIS pH 8.3; 50 mM KCl and 0.05 to 0.2 µM each primer. The amplifications are carried out in a thermocycler, an instrument that controls the temperatures and time required for the reaction. Thermocycling conditions consist of initial denaturation at 90 to 95° C. for two to five minutes followed by 30 cycles of denaturation at 90 to 95° C. for 30 to 60 seconds followed by primer annealing at a temperature of from 55 to 60° C. for 30 to 60 seconds and extension at 70 to 74° C. for 30 seconds. A final extension at 70 to 74° C. for up to 45 minutes can be made. After amplification, PCR products are analyzed in an automated sequencing apparatus and the amplification patterns, the lengths of the PCR products in base pairs are evaluated using specific softwares provided with the equipment, and table is generated containing with the animal number and its respective genotype. Alternatively, vertical electrophoresis systems employing high-resolution polyacrylamide gels may be used, as described by Regitano and Tambasco (REGITANO, L. C. de A.; TAMBASCO, D. D. Protocolo de análise de marcadores microssatelites. In: REGITANO, L. C. de A.; COUTINHO, L. L. (Org.). BIOLOGIA MOLECULAR APLICADA À PRODUçÃO ANIMAL. Brasília—DF, 2001, pp. 195-206) or real-time PCR may be used.

The present invention further relates to a method for the identification of animals having greater potential for meat quality traits by means of the analysis of specific markers.

In the following description, a number of terms are used extensively. The following definitions are provided to facilitate understanding of the invention.

The term "isolated nucleic acid molecule" is used herein to refer to the nucleic acids of the present invention. When this term is used to refer to the DNA of the present invention, it means isolated DNA markers of the DDEF1 gene, which are described in SEQ ID No. 1, SEQ ID No. 2, SEQ ID No. 3 or SEQ ID No. 4. For example, the "isolated nucleic acid molecule" may be used in amplification reactions in order to diagnose a certain material.

The term "oligonucleotide" is herein referred to as 'primers' and 'probes' of the present invention and is defined as a nucleic acid molecule comprising about 20 nucleotides. The exact size of the primers/probes will depend on various particular experimental factors of each step of the process. Oligonucleotides are often used as probes to detect complementary DNA or RNA.

The term "specifically hybridize" refers to the association between two single-stranded nucleic acid molecules of sufficiently complementary sequence to permit such hybridization under pre-determined conditions generally described in the art. In particular, the term refers to hybridization of an oligonucleotide with a substantially complementary sequence contained within a single-stranded DNA or RNA molecule of the present invention. Appropriate conditions enabling specific hybridization of single stranded nucleic acid molecules of varying complementarity are well known in the art. One common formula for calculating the stringency conditions required to achieve hybridization between nucleic acid molecules is as follows (Sambrook J., Fritsch E. F., and Maniatis T) Molecular Cloning, A Laboratory Manual, 2nd ed. 1989, Cold Spring Harbor Laboratory Press):

$$Tm=81.5° C.+16.6 \text{ Log } [Na+]+0.41(\% G+C)-0.63 \\ (\%\text{formamide})-600/\#bp \text{ in duplex(probe)}.$$

As an illustration of the above formula, using [Na+]= [0.368] and 50% formamide, with GC content of 42% and an average probe size of 200 bases, the Tm is 57° C.

The term "probe" as used herein refers to an oligonucleotide, polynucleotide or nucleic acid, either RNA or DNA, whether occurring naturally as in a purified restriction enzyme digest or produced synthetically, which is capable of annealing with or specifically hybridizing to a nucleic acid with sequences complementary to the probe. A probe may be either single-stranded or double-stranded. The exact length of the probe will depend upon many factors, including temperature, source of probe and use of the method. For example, depending on the complexity of the target sequence, the oligonucleotide probe typically contains about 15 to 25 or more nucleotides, although it may contain fewer nucleotides. The probes herein may be selected to be complementary to different strands of a particular target nucleic acid sequence. This means that the probes must be sufficiently complementary so as to be able to "specifically hybridize" or anneal with their respective target strands under a set of pre-determined conditions. Therefore, the probe sequence need not reflect the exact complementary sequence of the target. For example, a non-complementary nucleotide fragment may be attached to the 5' or 3' end of the probe, with the remainder of the probe sequence being complementary to the target strand. Alternatively, non-complementary bases or longer sequences can be interspersed into the probe, provided that the probe sequence has sufficient complementarity with the sequence of the target nucleic acid to anneal therewith specifically.

The term "primer" as used herein refers to an oligonucleotide, either RNA or DNA, either single-stranded or double-stranded, either derived from a biological system, generated by restriction enzyme digestion, or produced synthetically which, when placed in the proper environment, is able to functionally act as an initiator of template-dependent nucleic acid synthesis. When presented with an appropriate nucleic acid template, suitable nucleoside triphosphate precursors of nucleic acids, a polymerase enzyme, suitable cofactors and conditions such as appropriate temperature and pH, the primer may be extended at its 3' terminus by the addition of nucleotides by the action of a polymerase or similar activity to yield a primer extension product. The primer may vary in length depending on the particular conditions and requirement of the application. For example, in diagnostic applications, the oligonucleotide primer is typically about 15-25 or more nucleotides in length. The primer must be of sufficient complementarity to the desired template to prime the synthesis of the desired extension product. It is not required that the primer sequence represent an exact complement of the desired template. For example, a non-complementary nucleotide sequence may be attached to the 5' end of an otherwise complementary primer. Alternatively, non-complementary bases may be interspersed within the oligonucleotide primer sequence, provided that the primer sequence has sufficient complementarity with the sequence of the desired template strand to functionally provide a template-primer complex for the synthesis of the extension product.

The term "molecular marker" as used herein refers to a particular DNA segment (corresponding to expressed or non-expressed regions of the genome) which identifies DNA variability related to a desirable characteristic, that allows one to locate its position in the chromosome. The molecular markers of the present invention are those selected from the group consisting of SEQ ID No. 1, SEQ ID No. 2, SEQ ID No. 3 or SEQ ID No. 4. Currently, large-scale genotyping allows the analysis of thousands of markers simultaneously. Such large-scale analysis may be used, e.g., for genomic selection.

The term "gene" means a specific nucleotide sequence located in a particular region of the chromosome that is responsible for encoding a specific end product. The gene also carries in its primary structure all the information required for transcription and translation biological processes, such as for example, promoters and transcription regulatory regions.

The term "bovines", as used herein refers to the mammal, ruminant, artiodactyl animal having a pair of unbranched, hollow, permanent horns that belongs to the genus *Bos*, which includes species domesticated by humans. Preferably, the present invention refers to *Bos indicus* bovines.

The terms "PCR" or "amplification" refer to the polymerase chain reaction method, which enables the production of multiples copies of a gene or DNA fragment.

The present invention uses the PCR method to amplify a fragment containing intron 13 of the DDEF1 gene that harbors the polymorphism that was shown to be associated with different production traits.

The term "genetic variant" relates to the different combinations of nucleotide sequences that may exist for the same genomic region, also known as alleles of a locus.

The present invention uses experimental identification of a significant association of genotypes of the centromeric region of BTA 14 with rib eye area (REA), weaning weight and 18-month weight.

The invention concerns isolated nucleic acid molecules characterized by being sequences selected from the group consisting of SEQ ID No. 1, SEQ ID No. 2, SEQ ID No. 3 or SEQ ID No. 4. These molecules may be used as molecular markers.

The method of the present invention consists of the following steps: (i) extracting DNA from the animals having potential for desirable characteristics of meat production; (ii) genotyping the DDEF1 gene; (iii) identifying in the genomic sequence as set forth in (ii) the genotype or genotypes or the genetic variant associated with rib eye area (REA), weaning weight and 18-month weight, and (iv) establishing an association between the genotype and the phenotype, taking into account the allelic frequencies of the population being studied.

DNA samples may be extracted from blood or semen of the animals. The extraction can be made according to procedures described by REGITANO (REGITANO, L.C.A. Introdução ao use de marcadores moleculares In: Regitano L. C. A. And Coutinho LL (Eds.) Biologic molecular aplicada à produção animal. Brasília: Embrapa Informação Tecnológica, 2001) or any procedure that enables access to the DNA within the cell nucleus, such as for example methods using organic solvents. Known conditions and reagents are used in the DNA extraction step, such as for example, the extraction carried out according to Regitano (REGITANO, L. C.de A.; TAMBASCO, D. D. Protocolo de análise de marcadores microssatelites. In: REGITANO, L. C. de A.; COUTINHO, L. L. (Org.). BIOLOGIA MOLECULAR APLICADA À PRODUçÃO ANIMAL. Brasília—DF, 2001, pp. 195-206) which comprises treating whole blood with a solution that promotes lysis of red cells to obtain leucocytes; disrupting the leukocytes thus obtained in the presence of a detergent such as SDS (sodium dodecyl sulfate) and a proteolytic enzyme such as Proteinase K; removing the proteins from the solution by precipitation in the presence of a high concentration of ions such as $Na^+Cl^-$; precipitating the DNA in the presence of an alcohol such as ethanol or isopropanol and re-hydrating it in an aqueous solution, preferably, Tris-EDTA buffer. Proteins may be alternatively excluded from the solution by organic solvents, such as phenol in the presence or not of chloroform and isoamyl alcohol. It is also possible to use filtration through a cellulose column followed by elution of DNA that has adhered thereto.

In vivo measurement of the rib eye area should be made using ultrasound measurements between the $12^{th}$ and the $13^{th}$ rib of the animal, above the longissimus muscle, these measurements being made when the animals are between 18 and 20 months of age, since after that the vertebral transverse processes become more pronounced, making it impossible to fit correctly the ultrasound probe for a more accurate measurement.

To that end, the animals are placed in a squeeze chute for obtaining ultrasonographic images using ultrasound equipment. Images providing REA measurements from the transversal section of the Longissimus muscle are analyzed and interpreted to obtain REA values in square centimeters ($cm^2$).

Animals should be weighed after weaning and then at the age of 16 to 18 months for obtaining the weaning and 18-month weights, respectively.

The genotyping set forth in step (ii) of the method may be performed using sequences selected from the group consisting of SEQ ID No. 1, SEQ ID No. 2, SEQ ID No. 3 or SEQ ID No. 4.

Genotyping for the SNP in the DDEF1 gene can be performed by PCR-ARMS, such as for example, employing preferably the primers listed in table 1 above.

Additional techniques may be used for the genotyping of this SNP, such as for example, real-time PCR using TaqMan™ detection system, in which primers and a probe pairing with the DNA target region enable the identification of different alleles.

The SNPs sequences are amplified using the PCR technique. Preferably, the present invention uses 20 to 200 ng of genomic DNA; 0.1 to 0.3 mM dNTPs; 1 to 2.0 mM $MgCl_2$; 20 mM TRIS pH 8.3; 50 mM KCl and 0.05 to 0.2 μM each primers. (THE FOUR PRIMERS ARE USED FOR AMPLIFYING INTRON 13 REGION OF THE DDEF1 GENE AND FOR RECOGNIZING DIFFERENT SNP ALLELES). The amplifications are carried out in a thermocycler, an instrument that controls the temperatures and time required for the reaction. Thermocycling conditions consist of initial denaturation at 90 to 95° C. for two to five minutes followed by 30 cycles of denaturation at 90 to 95° C. for 30 to 60 seconds followed by primer annealing at a temperature of from 55 to 60° C. for 30 to 60 seconds and extension at 70 to 74° C. for 30 seconds. A final extension at 70 to 74° C. for up to 45 minutes can be made. After amplification, PCR products are analyzed in an automated sequencing apparatus and the amplification patterns and lengths of the PCR products in base pairs are evaluated using specific softwares provided with the equipment. A table is generated containing the animal number and its respective genotype. Alternatively, vertical electrophoresis systems employing high-resolution polyacrylamide gels may be used, as described by Regitano and Tambasco (REGITANO, L. C. de A.; TAMBASCO, D. D. Protocolo de análise de marcadores microssatelites. In: REGITANO, L. C. de A.; COUTINHO, L. L. (Org.). BIOLOGIA MOLECULAR APLICADA À PRODUçÃO ANIMAL. Brasília—D F, 2001, pp. 195-206) or real-time PCR may be used.

The identification of step (iii) may be alternatively carried out in a genetic variant of the said genotype or genotypes. The identification of step (iii) may be performed using a SNP analysis method that may be selected from the group consisting of, but not limited to, PCR-RFLP (Restriction fragment length polymorphism), mass spectrometry, sequencing, High Resolution Melting, TaqMan allele-specific probe and, optionally, amplification with allele-specific primers (ARMS-PCR).

PCR products are preferably analyzed (genotyping) using different electrophoresis systems. Preferably, analyses are carried out in an ABI 3100 Avant sequencer (Applied Biosystems). Genotypes may be determined using GeneScan (version 3.7.1) and Genotyper (version 3.7) softwares. Genotyping may also be performed by any SNP analysis method, such as PCR-RFLP, mass spectrometry, sequencing, High Resolution Melting, or using allele-specific probes (TaqMan).

The establishment of an association between the genotype and the phenotype may be carried out by a statistical method correlating allele frequencies in the population being studied with the data distribution of a sample of the population from which the genotype is selected, either using analysis of variance, in which the response variable is the phenotypic trait and the genotypes for the marker are fixed effects, or using regression analysis with a coefficient for the number of copies of a certain allele represented in the genotype of each animal. Bayesian estimators, least-squares method, restricted maximum likelihood may be used for the analyses and they may or may not consider the covariance between related subjects (animal model). In the present invention the statistical methodology is preferably carried out by the method of restricted maximum likelihood in an animal model. Genotype x phenotype association may vary depending on the breed/population being studied, i.e., the same genotype may be positively associated in one population, but negatively associated in another. Therefore, determination of which genotype must be selected is only possible after the appropriate statistical method is employed taking into account allele frequencies of the population being studied and the data distribution of a sample of the population where the diagnostic method is intended to be used.

Identification of the genotype or genotypes or the genetic variant is associated with the rib eye area (REA), the weaning weight and the 18-month weight.

The invention is also embodied in the form of a kit for the identification of animals having a greater tendency for desirable characteristics in meat production, which is characterized by comprising: (i) suitable primers for the amplification of a portion of a DDEF1 gene sequence; (ii) reagents used in the genotyping reaction; and (iii) a manual containing instructions for the identification and interpretation of the results. The desirable characteristics in meat production are preferably rib eye area (REA), weaning weight and 18-month weight.

The primers used in the kit are sequences selected from the group consisting of SEQ ID No. 1, SEQ ID No. 2, SEQ ID No. 3 or SEQ ID No. 4.

The reagents used in the kit are those used in genotyping reactions, which are selected from Tris-HCl, KCl, DMSO, $MgCl_2$, dNTP, Taq DNA polymerase, and the like.

The invention is further characterized by using specific molecular markers selected from the group of SEQ ID No. 1, SEQ ID No. 2, SEQ ID No. 3 or SEQ ID No. 4 in the recognition of the single-nucleotide polymorphism that is associated with the following traits: rib eye area, weaning weight and 18-month weight in animals. The use of these markers is characterized by the fact that the single base polymorphism is located in intron 13 of the DDEF1 gene.

The method and the kit of the present invention may be used to identify animals raised on pasture and finished in feedlot. Preferably, the identification method and kit of the present invention are used in bovines, Canchim and Nellore breeds being preferred.

EXAMPLES

The invention will now be described in greater detail by means of the following examples, which should not be construed as a limitation on the scope of the invention.

Example 1

Material Collection and DNA Extraction

First, the fat thickness of 1171 animals of about 18 months of age was determined by ultrasound. The total mean value of subcutaneous fat thickness measurements was 1.94±0.79 mm, the minimum value obtained being 0.6 mm and the maximum value obtained being 5.4 mm.

Blood or semen samples were collected from all the animals evaluated for subcutaneous fat thickness and from parents of these animals for DNA extraction. 5 ml blood samples were collected by jugular vein or tail vein puncture into vacuum blood collection tubes containing 50 µl of 15% potassium EDTA (K3) (to prevent clotting) and stored under refrigeration until the DNA extraction process was initiated. Semen samples of some reproductive animals were provided by farms in straws that were kept frozen until the DNA extraction process.

Extraction was carried out using procedures described by Regitano (2001) or any procedure that enables access to the DNA within the cell nucleus. After extraction the DNA was quantified in a spectrophotometer, was then diluted in water to a final concentration of 40 ng/µl and stored in a freezer at −30° C.

The quality of the DNA thus extracted was assessed in a spectrophotometer considering values in excess of 1.6 and in 1% agarose gel by the visualization of a single band.

Example 2

Identification of Polymorphisms

Based on the sequence deposited at the GenBank, 13 pairs of primers were designed flanking the exons that code for the main domains of DDEF1 protein.

To identify polymorphisms in the DDEF1 gene, the expected breeding values (EBV) for fat thickness were estimated for 113 sires, parents of the 1171 animals.

The sires were ranked according to the expected breeding value and accuracy and the six with the highest expected breeding value and the highest accuracy and the six with the lowest expected breeding value and the highest accuracy were chosen. DNA from these sires was used in amplification and sequencing reactions to identify polymorphisms in the 13 chosen regions of the DDEF1 gene.

Example 3

Primers Design

It was noted that the size of the DDEF1 gene would make the complete sequencing thereof difficult. Therefore, the main conserved domains of the protein encoded by this gene were identified and the coding regions of said domains were located in the nucleotide sequence of the gene. They are the following: Centaurin Plekstrin Homology domain—PH/centaurin, ankyrin repeats (ANK), Src homology 3 domain—SH3 and ArfGap. The bases that code for these domains were identified in the mRNA. Thereafter, the regions corresponding to such domains were located in the genome sequence.

Based on this information, it was found that the exons encoding the five conserved domains were very spaced from each other. Thus, a set or sets of exons could not be amplified simultaneously and 13 pairs of primers were designed (one for each exon).

The primers were designed using Primer3 software and to prevent loss of quality of the exon regions, primers were designed to amplify a small intronic segment before and after the exons of interest.

Primers' designations are listed in table 2:

TABLE 2

| Designation of the primers | | |
| --- | --- | --- |
| Domain/Region | Exons | Designation |
| PH Centaurin | 13 | RP1 |
| PH Centaurin | 14 | RP2 |
| PH Centaurin | 15 | RP3 |
| PH Centaurin | 16 | RP4 |
| PH Centaurin | 17 | RP5 |
| ArfGap | 17 | RP5 |
| ArfGap | 18 | RAG2 |
| ArfGap | 19 | RAG3 |
| ArfGap | 20 | RAG4 |
| ANK | 21 | RA1 |
| ANK | 22 | RA2 |
| ANK | 23 | RA3 |
| SH3 | 30 | RS1 |
| SH3 | 31 | RS2 |

The 13 pairs of primers designed to amplify the 4 domains are listed in table 3:

TABLE 3

Primers designed to amplify PH Centaurin, ArfGap, ANK and SH3 domains of DDEF1 gene

| Primer | Gene | Domain | Location | | Sequence | Amplicon (bp) | SEQ ID NO: |
|---|---|---|---|---|---|---|---|
| RP1 | DDEF1 | PH Centaurin | Exon 12, 13 | Left: Right: | ATTGCTCACCTGCCCAGTTT GCCTTCCTCAAACCACACAT | 517 | 5 6 |
| RP2 | DDEF1 | PH Centaurin | Exon 14 | Left: Right: | TAATAAACGGCAGCCCAGAC CCCCACATGTTAAACACACG | 323 | 7 8 |
| RP3 | DDEF1 | PH Centaurin | Exon 15 | Left: Right: | CGCACAGTTAAAAGCCATTG CCAGCATACACCTCCTCTCA | 899 | 9 10 |
| RP4 | DDEF1 | PH Centaurin | Exon 16 | Left: Right: | GCTGAAACAAAAAGGTGCAA ACAGCTAAGCAGGGGAAACC | 322 | 11 12 |
| RP5 | DDEF1 | PH Centaurin | Exon 17 | Left: Right: | TTCCCTCCTGTTACTGCTTGA CTCCACGTCCATAATGCTGA | 488 | 13 14 |
| R2AG | DDEF1 | ArfGap | Exon 18 | Left: Right: | GGGTGTTTCATAGGCCTCAC CATGATTCGCCAGTTCTTCA | 557 | 15 16 |
| R3AG | DDEF1 | ArfGap | Exon 19 | Left: Right: | CATGGTTCCACCAGTCCATT CGATTGAAGCCACTGAACAA | 506 | 17 18 |
| R4AG | DDEF1 | ArfGap | Exon 20 | Left: Right: | TCAGCTGGAATGTTGAAGAGAA TAACAGCAGCCCCTTTCAGT | 466 | 19 20 |
| R1A | DDEF1 | ANK | Exon 21 | Left: Right: | TGAAAGGGGCTGCTGTTAAT TGGCCATGCTCACTTGTTTA | 408 | 21 22 |
| R2A | DDEF1 | ANK | Exon 22 | Left: Right: | TCGTCTTCCCTGCCTCTAAG GAATGGGCATGTCTCAGTTG | 476 | 23 24 |
| R3A | DDEF1 | ANK | Exon 23 | Left: Right: | ATGCCCATTCCGTTGTACTC GTGCTGGCCTGAATTTCTTT | 296 | 25 26 |
| R1S | DDEF1 | SH3 | Exon 30 | Left: Right: | CCGTGATGTTTGCTCTCAGAT GGGCCAGTGTTGAATGAGTT | 379 | 27 28 |
| R2S | DDEF1 | SH3 | Exon 31 | Left: Right: | GGTCATCGTGTCCTCCTTTC GGGCCAGTGTTGAATGAGTT | 550 | 29 30 |

Figure 2:
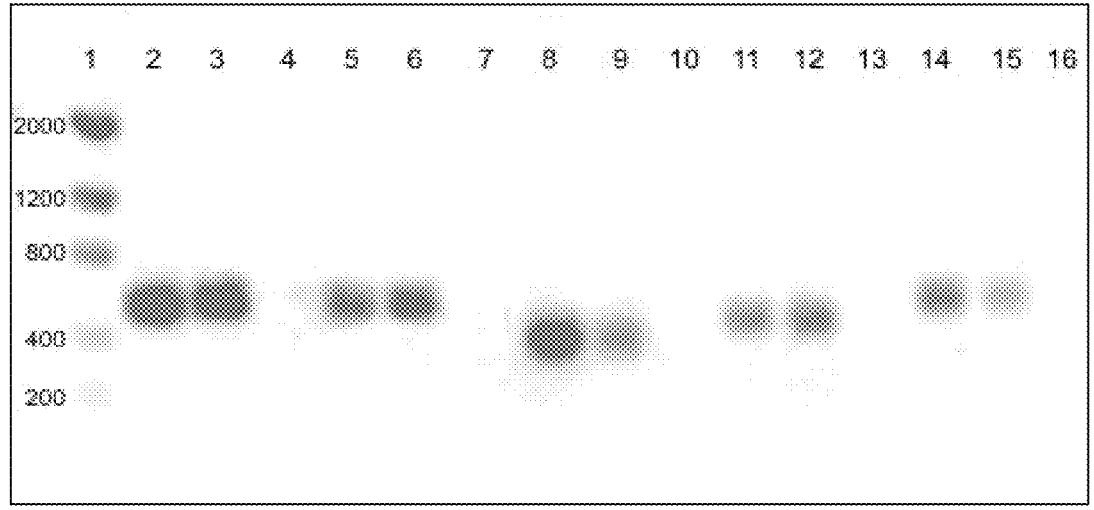
FIG. 2. 1% agarose gel for viewing the amplified fragments. Lane 1 corresponds to the low-mass DNA molecular weight ladder and lanes 2 to 16 correspond, respectively, to amplicons generated with R3AG, R3AG, R3AG negative, R4AG, R4AG, R4AG negative, R4P, R4P, R4P negative, R3P, R3P, R3P negative, R5P, R5P and R5P negative primers.

The specificity of the primers was confirmed by loading the PCR product obtained with the use of these primers in 1% agarose gel, which permits the visualization of a single band for each amplification product (FIGS. 1 and 2).

Example 4

Amplification of the Fragments

RA1, RA2, RP2, RP3, RP4, RP5, RAG2 primers were used in a reaction containing 200 ng of genomic DNA, 10 mM Tris-HCl (pH 8.3), 1.95 mM $MgCl_2$, 50 mM KCl, 200 µM each dNTP, 0.165 µM each primer and 1.3 units of Taq DNA polymerase to a final reaction volume of 30 µl. RP1, RAG3, RAG4, RS1, RS2, RA3 primers were amplified under the same conditions, except for the $MgCl_2$ concentration, which was 1.5 mM.

The amplification reaction consisted of an initial denaturation at 94° C. for 2 minutes followed by 35 cycles of denaturation at 94° C. for 30 seconds, annealing at the specific temperature for each primer for 30 seconds and extension at 72° C. for 30 seconds. After 35 cycles, the amplicon was subjected to a final extension for 10 minutes.

Annealing temperatures for each primer are listed in table 4:

TABLE 4

Annealing temperatures of the primers

| Annealing temperature | Primers |
|---|---|
| 54.1° C. | RA1, RP1 |
| 55.0° C. | RA2, R3AG, R4AG |
| 55.4° C. | RP4, RP3, RP5, RS2 |
| 53.0° C. | RP2, RAG2, RA3, RS1 |

Electrophoresis on 1% agarose gel stained with ethidium bromide was performed for the investigation of specific amplification. TBE 1× buffer (90 mM Tris base, 90 mM boric acid and 2 mM EDTA pH 8.0) and a voltage of 3 V/cm were used. A 5 µl volume of each amplification product was loaded to the gel with 1 µl of loading buffer (Glycerol, TBE 10×, 1% bromophenol blue, deionized water). After the electrophoresis was concluded, amplicons were visualized under ultraviolet illumination.

PCR reactions were purified using Wizard SV gel and PCR clean-up system kits. Purified PCR products were quantified in a spectrophotometer and diluted to a final concentration of 32 ng/µl.

Example 5

Sequencing of the Fragments

Sequencing reactions were carried according to a modification of the protocol described by Regitano et al. 2007 using ABI PRISM® Big Dye terminator v. 3.1 cycle sequencing Kit from Applied. Each reaction consisted of: 2 µL of water, 2 µL Big dye (DNA polymerase, dNTPs and ddNTPs), 2 µL buffer ($Mg^{+2}$ and Tris-HCl), 2 µL primer (2 µmol), 2 µL of the PCR product (32 ng/µL).

The sequencing reaction conditions were as follows: pre-incubation at 94° C. for 2 minutes; amplification in 25 cycles at 96° C. for 20", at a specific temperature (° C.) for each primer for 10" (according to table 2) and at 60° C. for 04'; cooling at 4° C. for ∝.

Each DNA strand of the analyzed regions was sequenced twice.

The sequencing products were purified and precipitated to prevent the non-incorporated ddNTPs, dNTPs, primers and enzyme from interfering in the sequencer reading. 40 µL of 65% isopropanol were added at room temperature. The mixture was vortexed for a few seconds and incubated in the dark at room temperature (RT) for 15 minutes. Next, it was centrifuged for 25 minutes at 14000 rpm at RT. The supernatant was discarded by inverting the flask, 200 µL of 60% ethanol were added at room temperature and centrifuged for 5 minutes at 14,000 rpm at RT. The supernatant was discarded by inverting the flask (washing with 60% ethanol was repeated twice). The reactions were allowed to dry in the dark for 1 hour and then were stored in a freezer at −20° C. (modification of the method by Regitano 2007).

Products of the sequencing reactions were analyzed in an ABI 3100 Avant sequencer (Applied Biosystems). Sequencing electropherograms were analyzed using Phred, Phrap and Consed softwares in order to choose good quality sequences and to visualize the possible polymorphisms occurring in subjects who are heterozygous thereto. Clustal W software was used to identify polymorphisms occurring among homozygous subjects. Based on the SNPs data, locations thereof within the genomic sequence of the full-length gene were identified. 12 bulls were genotyped for all the SNPs identified, and then a Fisher's exact test was used to evaluate the allele frequency distribution among bulls with extreme genetic values for subcutaneous fat thickness. It was investigated whether the SNPs present in exons would result in amino acids changes in the protein.

A Fisher's exact test was performed for each SNP found so as to verify the predominance of one allele of a given SNP in one of the extremes for fat thickness according to the expected breeding value. This test was chosen over the Qui_square test for being more appropriate for Ns of less than 20. The SNP having the lowest p-value was chosen for validation in the offspring of Canchim bulls used for the SNPs identification.

73 polymorphisms in the DDEF1 gene were identified, 13 of them being located within exons. The Fisher's exact test showed a p-value=0.0167 for a SNP located in intron 13 of the DDEF1 gene at 279401 by position (table 5), and it was tested in a population of 987 animals and the association thereof was validated.

TABLE 5

Results of the Fisher's exact test for all regions of the DDEF1 gene analyzed, being ranked in descending order according to the p-values.

| Gene | Region | Location in the DDEF1 gene (bp) | Gene region | Sequence | Genotype | P |
|---|---|---|---|---|---|---|
| DDEF1 | RP1 | 279401 | Intron 13 | TCCATGA | A/G | 0.0167* |
| DDEF1 | RP1 | 279348 | Intron 13 | TCCGTGG | G/A | 0.032* |
| DDEF1 | R4AG | 302474 | Intron 21 | GTAACAG | A/C | 0.0466* |
| DDEF1 | RP1 | 279523 | Intron 14 | GTATGTC | T/C | 0.0706□ |
| DDEF1 | RP3 | 289841 | Intron 16 | TCCTGGG | T/C | 0.0829□ |
| DDEF1 | RP1 | 279709 | Intron 14 | CTGATCT | A/G | 0.0888□ |
| DDEF1 | RP3 | 289810 | Exon 15 | TTTCGAC | C/T | 0.0888□ |
| DDEF1 | RP1 | 279578 | Intron 14 | AGTGACC | G/A | 0.1087□ |
| DDEF1 | R4AG | 302359 | Exon 20 | ATCAGCT | A/T | 0.1087□ |
| DDEF1 | R3AG | 298921 | Intron 19 | TGCGTTT | G/A | 0.1398 |
| DDEF1 | RP3 | 289636 | Intron 15 | TTATCGA | T/C | 0.1555 |
| DDEF1 | R1S | 335016 | Intron 31 | TGCATGG | A/G | 0.1555 |
| DDEF1 | R1AG | 295329 | Intron 18 | ACCCGTG | C/T | 0.1635 |
| DDEF1 | RP3 | 289729 | Intron 15 | TCATGTC | T/C | 0.2391 |
| DDEF1 | R2AG | 297005 | Intron 19 | TACAAAG | A/C | 0.2391 |
| DDEF1 | R4AG | 302361 | Exon 20 | GAACGAA | C/T | 0.2391 |
| DDEF1 | R1S | 334712 | Intron 30 | GGCCCTT | C/T | 0.2391 |

TABLE 5-continued

Results of the Fisher's exact test for all regions of the DDEF1 gene analyzed, being ranked in descending order according to the p-values.

| Gene | Region | Location in the DDEF1 gene (bp) | Gene region | Sequence | Genotype | P |
|---|---|---|---|---|---|---|
| DDEF1 | R1S | 334730 | Intron 30 | GCACCCA | C/T | 0.2391 |
| DDEF1 | R1S | 334788 | Intron 30 | GCTCGGC | C/T | 0.2391 |
| DDEF1 | RP1 | 279388 | Intron 13 | GGCATGA | A/T | 0.2484 |
| DDEF1 | R1AG | 295286 | Intron 18 | CACATAC | A/G | 0.2751 |
| DDEF1 | R2AG | 296691 | Intron 18 | GCTCCCT | C/A | 0.2998 |
| DDEF1 | RP1 | 279270 | Intron 12 | TCCACTA | A/G | 0.3 |
| DDEF1 | R2AG | 296832 | Exon 18 | GGGTATC | T/C | 0.3198 |
| DDEF1 | RP2 | 280457 | Intron 14 | GTGTTTG | T/A | 0.3332 |
| DDEF1 | R2A | 304307 | Intron 23 | CACTGGA | T/C | 0.3332 |
| DDEF1 | RP2 | 280466 | Intron 14 | TCCATCC | A/G | 0.3416 |
| DDEF1 | RP3 | 289610 | Intron 15 | AGTATTC | A/G | 0.3416 |
| DDEF1 | R2AG | 296805 | Exon 18 | AGAACCCT | A/G | 0.3416 |
| DDEF1 | RP3 | 289705 | Intron 15 | GCGTTT | G/A | 0.3416 |
| DDEF1 | R2AG | 297037 | Intron 19 | TGCGTAG | G/A | 0.3416 |
| DDEF1 | R3AG | 298842 | Intron 19 | GAGGGAA | G/A | 0.3416 |
| DDEF1 | RP5 | 295091 | Exon 17 | GACGAAC | G/A | 0.3633 |
| DDEF1 | RP1 | 279616 | Intron 14 | GACGCAC | G/A | 0.3913 |
| DDEF1 | RP2 | 280448 | Intron 14 | TATTGGG | T/C | 0.3913 |
| DDEF1 | RP2 | 280559 | Intron 15 | GCTTGTT | T/C | 0.3913 |
| DDEF1 | RP3 | 289777 | Exon 15 | CCAGGTG | G/A | 0.3913 |
| DDEF1 | R3AG | 299102 | Intron 20 | TTCATGG | A/G | 0.3913 |
| DDEF1 | R4AG | 302193 | Intron 20 | CTTGGCG | G/C | 0.3913 |
| DDEF1 | R1A | 302926 | Intron 22 | GGTATCT | A/G | 0.3913 |
| DDEF1 | R2A | 304153 | Exon 22 | CCTAGAT | A/G | 0.3913 |
| DDEF1 | RP5 | 295041 | Intron 17 | GCACTCA | C/T | 0.3973 |
| DDEF1 | RP5 | 294998 | Intron 17 | TCCGAGT | G/A | 0.4 |
| DDEF1 | RP5 | 295067 | Intron 17 | TGGCGGC | C/T | 0.4 |
| DDEF1 | R1AG | 295211 | Exon 17 | CGACGTC | C/T | 0.4 |
| DDEF1 | R1AG | 295277 | Intron 18 | CACGCCC | G/A | 0.4 |
| DDEF1 | R1AG | 295316 | Intron 18 | TCCGAGT | G/A | 0.4 |
| DDEF1 | RP3 | 289732 | Intron 15 | TGTCCAG | C/T | 0.4099 |
| DDEF1 | R2AG | 296709 | Intron 18 | CTTTCCC | T/C | 0.4099 |
| DDEF1 | R2AG | 296728 | Intron 18 | AAAATTT | A/T | 0.4099 |
| DDEF1 | R3AG | 298765 | Intron 19 | ACTATCT | A/C | 0.4099 |
| DDEF1 | R3AG | 299072 | Intron 20 | TAACTGT | C/T | 0.4099 |
| DDEF1 | R4AG | 302287 | Exon 20 | GACCGTA | C/T | 0.4099 |
| DDEF1 | RP2 | 280615 | Intron 15 | AGCGCAT | G/T | 0.4545 |

TABLE 5-continued

Results of the Fisher's exact test for all regions of the DDEF1 gene analyzed, being ranked in descending order according to the p-values.

| Gene | Region | Location in the DDEF1 gene (bp) | Gene region | Sequence | Genotype | P |
|---|---|---|---|---|---|---|
| DDEF1 | R4AG | 302353 | Exon 20 | ATCCTCA | C/T | 0.4545 |
| DDEF1 | RP5 | 295023 | Intron 17 | AACGCAG | G/A | 0.4632 |
| DDEF1 | RP5 | 295106 | Exon 17 | GGAGGCC | G/A | 0.4632 |
| DDEF1 | R1AG | 295266 | Intron 18 | GCACGCC | C/T | 0.4632 |
| DDEF1 | R1AG | 295293 | Intron 18 | TCCCAAC | C/G | 0.4632 |
| DDEF1 | RP1 | 279481 | Exon 13 | CGGCAGC | C/T | 0.5 |
| DDEF1 | RP1 | 279624 | Intron 14 | TTACAGT | C/G | 0.5 |
| DDEF1 | R2AG | 296675 | Intron 18 | AGTTTTA | T/C | 0.5 |
| DDEF1 | R2AG | 296765 | Intron 18 | CACTCTA | T/A | 0.5 |
| DDEF1 | R3AG | 299054 | Intron 20 | GAATTCT | T/A | 0.5 |
| DDEF1 | R2A | 304327 | Intron 23 | AAACTCC | C/T | 0.5 |
| DDEF1 | R3A | 304683 | Intron 24 | GGGCGTT | C/T | 0.5 |
| DDEF1 | R1S | 335110 | Intron 31 | CTTATCA | A/G | 0.5 |
| DDEF1 | RP3 | 289874 | Intron 16 | CCCATTC | A/G | 0.5217 |
| DDEF1 | RP4 | 291964 | Intron 17 | CACGGCA | G/A | 0.5217 |
| DDEF1 | R2AG | 296956 | Intron 19 | TCACGAA | C/T | 0.5217 |
| DDEF1 | R4AG | 302428 | Exon 20 | TGCAGAG | A/C | 0.5217 |
| DDEF1 | R4AG | 302499 | Intron 21 | GAGGAGG | G/C | 0.5217 |
| DDEF1 | R1AG | 295321 | Intron 18 | GTGCGGT | C/T | 0.6 |

*p ≥ 0.05

A restricted maximum likelihood analysis showed an indicative association (p≤0.07) between the SNP of the DDEF1 gene (table 6) and subcutaneous fat thickness in the population studied. This marker had a significant allele-substitution effect (p=0.027) (table 7). A positive value for the additive effect implies that the allele causes an increase in the phenotypic mean. Allele A would increase the mean fat thickness over the homozygous G by 0.063 mm in the population studied (table 7).

TABLE 6

Results of the restricted maximum likelihood analysis

| | DDEF1 SNP | |
|---|---|---|
| Effect | DF | p-value |
| Mean | 1 | <0.01 |
| CG | 32 | <0.01 |
| DDEF1 SNP | 2 | 0.071 |
| Age | 1 | <0.01 |

CG = contemporary groups;
DF = degrees of freedom;
p = Likelihood associated with the variance ratio test

TABLE 7

Results of the analysis of the allele-substitution effect of DDEF1 marker on subcutaneous fat thickness in Canchim and estimate for determining the contribution of the DDEF1 marker allele A in the phenotype

| | DDEF1 marker | | Allele effect (mm) |
|---|---|---|---|
| Effect | DF | p-value | |
| Mean | 1 | <0.01 | — |
| CG | 32 | <0.01 | — |
| Allele A | 1 | 0.027 | 0.06322 |
| Allele G | — | — | — |
| Age | 1 | <0.01 | — |

CG = contemporary groups;
DF = degrees of freedom;
P = Likelihood associated with the variance ratio test This association may vary depending on the breed/population being studied. Therefore, determination of which genotype must be selected is only possible after the appropriate statistical method is employed taking into account allele frequencies of the population being studied and the phenotypic data distribution of a sample of the population where the diagnostic method is intended to be used.

Example 6

Animal Selection

Bulls were selected from catalogs of the main artificial insemination centers in the country. 20 bulls active in the population were chosen from a total of 616 Nellore polled and horned bulls to be part of the sample, i.e., those whose semen is available in the market for values not exceeding R$50.00, to represent bulls that are affordable to the typical breeder having genealogies representative of the main lineages of the Nellore Breed, which are more frequently commercialized. Animals were chosen so as to minimize the degree of relationship among them.

Example 7

Samples Collection and DNA Extraction

Samples used for DNA extraction were straws of frozen semen provided by artificial insemination centers. DNA was extracted using a salting out procedure with organic solvents (phenol, chloroform and isoamyl alcohol.

5 mL blood samples were collected by jugular vein puncture into potassium EDTA (K3)-containing vacuum collection tubes from calves descending from the 30 bulls. Samples were stored under refrigeration until the extraction process was initiated. DNA extraction was carried out from leukocytes using the salting out method according to Regitano (REGITANO, L. C. de A.; TAMBASCO, D. D. Protocolo de análise de marcadores microssatelites. In: REGITANO, L. C. de A.; COUTINHO, L. L. (Org.). BIOLOGIA MOLECULAR APLICADA À PRODUçÃO ANIMAL. Brasília—DF, 2001, pp. 195-206).

Example 8

Measurement of Rib Eye Area

In vivo REA measurements were made in animals of about 18 months of age. PieMedical Scanner 200 Vet equipment with linear array transducer of 18 cm and 3.5 MHz was used. Animals were placed in a squeeze chute to obtain ultrasonographic images. Images providing SFT (subcutaneous fat thickness) and REA measurements were obtained from the transversal section of the Longissimus muscle between the $12^{th}$ and the $13^{th}$ ribs. These images were analyzed and interpreted to obtain REA values in square centimeters ($cm^2$). ODT (Open data transfer) software, which is provided with the ultrasound equipment, was used for image analysis.

Example 9

Weighting the Animals

Animals were weighed after weaning, and then at the age of 16 to 18 months to obtain the weaning and 18-month weights, respectively. Weaning weights were fitted to 240 days and 18-month weights were fitted to 450 days according to the weight fitting formula used in Embrapa CNPGC breeding program.

The formula used to fit the weaning weight to 240 days was as follows:

$$\frac{PD - 30}{ID} \times 240 + 30$$

The formula used to fit the 18-month weight to 450 days was as follows:

$$\frac{PD - PD}{IS - ID} \times (450 - IS) + PS$$

$PD$ = Weaning weight $PS$ = 18-month weight $ID$ = Age at weaning $IS$ = Yearling age

Example 10

Measurement of Meat Tenderness

After slaughter, 2.5 cm steaks were taken from the longissimus muscle (striploin) between the $12^{th}$ and $13^{th}$ ribs. These steaks were identified, vacuum-packed and frozen for further analysis, if required.

The steaks were roasted in an electric oven at a temperature of 180° C. to evaluate meat tenderness. Internal temperatures of the steaks were measured using digital thermometers. Steaks were removed from oven when the thermometers reached 70° C. and after cooling, eight cylindrical-shaped pieces were excised in parallel to the muscle fibers using a cutter of 1.27 cm in diameter to determine the force required to transversely cut each cylindrical piece in an Texture Analyzer TA-XT2i coupled to a Warner-Bratzler blade with a thickness of 1.016 mm.

Tenderness measurements were made when the samples were delivered by the cold stores approximately 24 hours after slaughter.

Example 11

Polymorphism Genotyping

The DDEF1 gene SNP (DDEF1_g.279401A>G—access number: 181800428, disclosed by Veneroni et al. (VENERONI, G.B, MEIRELLES, S.L, GOUVEIA, J.J.S., SANTIAGO, A.C., OLIVEIRA, H.N., ALENCAR, M.M., REGITANO, L.C.A. Identificação de SNPs no gene DDEF1 bovino. In: 54° Congresso Brasileiro de Genética. Annals . . . Salvador. pp. 231, 2008) was genotyped according to an adaptation of the ARMS methodology by Buitkamp and Semmer (BUITKAMP, J. e SEMMER, J. A robust, low- to medium-throughput prnp genotyping system in sheep. BMC Infectious Diseases, v.4, pp. 30, 2004.).

PCR products were analyzed in an ABI 3100 Avant automatic DNA sequencer (Applied Biosystems). Genotypes were determined using GeneScan software (version 3.7.1).

Example 12

Effect of the Marker on REA

To study the effects of environmental and genetic factors on the carcass characteristic of REA, variance analyses were carried out using the method of least-squares that presents a statistical model including the effects of the contemporary group and the age at measurement covariate as fixed effects and the animal's father as a random effect. Six contemporary groups (CG) were formed based on the variables place of birth and birth month.

Table 8 depicts a summary of analyses of variance including the effect of the DDEF1 marker on REA. A significant association of p<0.05 was found between DDEF1 gene and REA.

TABLE 8

Summary of the analyses of variance including the effect of the DDEF1 marker on the rib eye area (REA) in Nellore cattle.
REA

| Source of variation | Degrees of Freedom | p-value |
| --- | --- | --- |
| CG | 5 | 0.092* |
| DDEF1 | 2 | 0.0203** |
| Age | 1 | 0.5587 |

GC = contemporary group;
DDEF1 = marker;
Age = Age of the animal at measurement;
*P < 0.10;
**P < 0.05.

There are no reports of an association between the DDEF1 gene and REA and the present document was the first to investigate this association and to observe a significant effect. REA is a characteristic correlated with muscularity and it may affect carcass quality. The association between a marker and REA may contribute to early selection, since this characteristic is measured later in life (when the animal reaches about 18 months of age or after slaughter), thereby contributing for animal breeding due to the inclusion of this characteristic in breeding programs.

An animal model with the contemporary group and genotypes as fixed effects and the age of the animal at measurement (linear effect) as a covariate as well as the bull as a random effect was used to evaluate the influence of the marker on REA. The analyses were made by the restricted maximum likelihood method (REML) using the PROC MIXED procedure from the Statistical Analysis System (SAS Institute Inc., 2000—SAS Institute Inc. SAS procedures guide. $8^{th}$ ed. Cary, 2000).

Example 13

Effect of the Marker on Weaning Weight and 18-Month Weight

To study the effects of environmental and genetic factors on the growth characteristics of weaning weight and 18-month weigh variance analyses were carried out using the method of least-squares. An animal model with the place of birth and genotypes as fixed effects and the age of the animal at weighting date (linear effect) as a covariate as well as the bull as a random effect was used to evaluate the influence of the marker on the characteristics. The analyses were made by the restricted maximum likelihood method (REML) using the PROC MIXED procedure from the Statistical Analysis System (SAS) (SAS Institute Inc., 2000—SAS Institute Inc. SAS procedures guide. $8^{th}$ ed. Cary, 2000).

Table 9 depicts a summary of the analyses of variance including the effect of the DDEF1 marker on weaning weight. A significant association p<0.05 was found between DDEF1 gene and the weaning weight.

TABLE 9

Summary of the analyses of variance including the effect of the DDEF1 marker on the weaning weight in Nellore cattle.
Weaning weight

| Source of variation | Degrees of Freedom | p-value |
| --- | --- | --- |
| Place of birth | 5 | <.0001*** |
| DDEF1 | 2 | 0.0159** |
| Age | 1 | <.0001*** |

Age = Age of the animal age at weighting date;
**p < 0.05;
***p < 0.01

Table 10 depicts a summary of the analyses of variance including the effect of the DDEF1 marker on the 18-month weight. A significant association p<0.01 was found between DDEF1 gene and the 18-month weight.

TABLE 10

Summary of the analyses of variance including the effect of the DDEF1 marker on the 18-month weight in Nellore cattle.
Weaning weight (18-month weight)

| Source of variation | Degrees of Freedom | p-value |
| --- | --- | --- |
| Place of birth | 5 | <.0001*** |
| DDEF1 | 2 | 0.0023*** |
| Age | 1 | 0.0503** |

Age = Age of the animal age at weighting date;
**p < 0.05;
***p < 0.01

No reports have been provided of an association between the DDEF1 gene and growth characteristics such as weaning weight and 18-month weight, therefore, the present document was the first to investigate this association and to observe a significant effect between these characteristics and the marker. Productive efficiency assessment is important for beef cattle exploitation and it may be quantified, for example, by the amount in kilograms of weaned calves per cow over the year, which reflects profitability of the herd.

The implementation of breeding programs that enable increased weight gains in animals is important, since the weaning weight serves to evaluate an individual's growth genetic potential as well as the cow's maternal ability (SOUZA, J.C.; RAMOS, A.A.; SILVA, L.O.C.; EUCLIDES FILHO, K.; ALENCAR, WECHSLER, F. S.; FERRAZ FILHO, P.B. Fatores ambientais sobre peso ao desmame de bezerros da raça Nelore em regiões tropicais brasileiras. Cienc. Rural, v. 30 n. 5, 2000). The 18-month weight may also be used as an indicator of genetic potential for growth in an individual. The identification of a marker associated with growth characteristics may aid in the selection of reproductive animals in order to produce more profitable herds and it may enable the establishment of a production profile for economically important characteristics since birth.

Example 14

Effect of the Marker on Meat Tenderness

An animal model using the fixed effects of genotypes and the contemporary group comprising the effects of place of birth, month of birth and slaughter batch, and the age of the animal at slaughter date (linear effect) and the pH as covariates as well as the bull as a random effect was used to evaluate the influence of the marker on the meat tenderness characteristic. The analyses were made by the restricted maximum likelihood method (REML) using the PROC MIXED procedure from the Statistical Analysis System (SAS) (SAS Institute Inc., 2000—SAS Institute Inc. SAS procedures guide. $8^{th}$ ed. Cary, 2000).

Only animals confined in Embrapa CPPSE were used in this analysis (total of 137 animals).

Table 11 depicts a summary of the analyses of variance including the effect of the DDEF1 marker on meat tenderness. A significant association p<0.01 was found between DDEF1 gene and meat tenderness.

TABLE 11

Summary of the analyses of variance including the effect of the DDEF1 marker on tenderness in Nellore cattle.
Meat tenderness

| Source of variation | Degrees of Freedom | p-value |
|---|---|---|
| CG | 17 | 0.0010*** |
| DDEF1 | 2 | 0.0083*** |
| pH | 1 | 0.0878* |
| Age | 1 | 0.0349** |

CG = contemporary group,
Age = animal's age at slaughtering,
*p < 0.10;
*p < 0.05;
***p < 0.01

A significant association (p<0.05) was found between the marker located in the DDEF1 gene and the characteristics of rib eye area (REA) and weaning weight, and a highly significant association (p<0.01) was found between the marker and the characteristics of 18-month weight and meat tenderness. Association studies between this gene and economically important traits for meat production in other bovine populations may aid to validate this association and to include this trait in breeding programs.

SEQUENCE LISTING

GENERAL INFORMATION:
   I.a) Applicant: EMPRESA BRASILEIRA DE PESQUISA AGROPECUÁRIA-EMBRAPA
   I.b) Address: Parque Estação Biológica PqEB, Av. W3 Norte (Final), Brasilia, DF
   II) Title of the invention: Method for the identification of animals
      having a greater potential for desirable characteristics of meat quality, rib
      eye area (REA), weaning weight and 18-month weight
   III) Sequences number: 32
   IV) Computer reading format:
 IV.a) Means used: CD.
 IV.b) Computer used: IBM PC compatible.
 IV.c) Operating system: PC-DOS/MS-DOS.

SEQUENCE GENERAL INFORMATION:
   I.a) Sequence identifying number: SEQ ID No. 01
   II) Sequence features:
 II.a) Size: 29
 II.b) Type: DNA
 II.c) Organism: artificial sequence
  III) Characteristic:
 III.a) other relevant information: primer for SNP genotyping
     ATATGGGAAT CCTAGAGAGG AGACGTAAC               29

I.a) Sequence identifying number: SEQ ID No. 02
   II) Sequence features:
 II.a) Size: 25
 II.b) Type: DNA
 II.c) Organism: artificial sequence
  III) Characteristic:
 III.a) other relevant information: primer for SNP genotyping
     GGGAATCCTA GAGAGGAGAC GTAAT                   25

I.a) Sequence identifying number: SEQ ID No. 03
   II) Sequence features:
 II.a) Size: 24
 II.b) Type: DNA
 II.c) Organism: artificial sequence
  III) Characteristic:
 III.a) other relevant information: primer for SNP genotyping
    GACTAGAAAT AGGAGACCCG GACC

24

I.a) Sequence identifying number: SEQ ID No. 04
   II) Sequence features:
 II.a) Size: 20
 II.b) Type: DNA
 II.c) Organism: artificial sequence
  III) Characteristic:
 III.a) other relevant information: primer for SNP genotyping
     GCCTTCCTCA AACCACACAT

SEQUENCE LISTING

```
20
   I.a) Sequence identifying number: SEQ ID No. 05
   II) Sequence features:
  II.a) Size: 20
  II.b) Type: DNA
  II.c) Organism: artificial sequence
  III) Characteristic:
 III.a) other relevant information: primer for SNP genotyping
        ATTGCTCACCTGCCCAGTTT 20
   I.a) Sequence identifying number: SEQ ID No. 06
   II) Sequence features:
  II.a) Size: 20
  II.b) Type: DNA
  II.c) Organism: artificial sequence
  III) Characteristic:
 III.a) other relevant information: primer for SNP genotyping
        GCCTTCCTCAAACCACACAT 20
   I.a) Sequence identifying number: SEQ ID No. 07
   II) Sequence features:
  II.a) Size: 20
  II.b) Type: DNA
  II.c) Organism: artificial sequence
  III) Characteristic:
 III.a) other relevant information: primer for SNP genotyping
        TAATAAACGGCAGCCCAGAC 20
   I.a) Sequence identifying number: SEQ ID No. 08
   II) Sequence features:
  II.a) Size: 20
  II.b) Type: DNA
  II.c) Organism: artificial sequence
  III) Characteristic:
 III.a) other relevant information: primer for SNP genotyping
        CCCCACATGTTAAACACACG 20
   I.a) Sequence identifying number: SEQ ID No. 09
   II) Sequence features:
  II.a) Size: 20
  II.b) Type: DNA
  II.c) Organism: artificial sequence
  III) Characteristic:
 III.a) other relevant information: primer for SNP genotyping
        CGCACAGTTAAAAGCCATTG 20
   I.a) Sequence identifying number: SEQ ID No. 10
   II) Sequence features:
  II.a) Size: 20
  II.b) Type: DNA
  II.c) Organism: artificial sequence
  III) Characteristic:
 III.a) other relevant information: primer for SNP genotyping
        CCAGCATACACCTCCTCTCA 20
   I.a) Sequence identifying number: SEQ ID No. 11
   II) Sequence features:
  II.a) Size: 20
  II.b) Type: DNA
  II.c) Organism: artificial sequence
  III) Characteristic:
 III.a) other relevant information: primer for SNP genotyping
        GCTGAAACAAAAAGGTGCAA 20
   I.a) Sequence identifying number: SEQ ID No. 12
   II) Sequence features:
  II.a) Size: 20
  II.b) Type: DNA
  II.c) Organism: artificial sequence
```

SEQUENCE LISTING

```
      III) Characteristic:
    III.a) other relevant information: primer for SNP genotyping
           ACAGCTAAGCAGGGGAAACC 20
      I.a) Sequence identifying number: SEQ ID No. 13
       II) Sequence features:
     II.a) Size: 21
     II.b) Type: DNA
     II.c) Organism: artificial sequence
      III) Characteristic:
    III.a) other relevant information: primer for SNP genotyping
           TTCCCTCCTGTTACTGCTTGA 21
      I.a) Sequence identifying number: SEQ ID No. 14
       II) Sequence features:
     II.a) Size: 19
     II.b) Type: DNA
     II.c) Organism: artificial sequence
      III) Characteristic:
    III.a) other relevant information: primer for SNP genotyping
           CTCCACGTCCATAATGCTGA 19
      I.a) Sequence identifying number: SEQ ID No. 15
       II) Sequence features:
     II.a) Size: 20
     II.b) Type: DNA
     II.c) Organism: artificial sequence
      III) Characteristic:
    III.a) other relevant information: primer for SNP genotyping
           GGGTGTTTCATAGGCCTCAC 20
      I.a) Sequence identifying number: SEQ ID No. 16
       II) Sequence features:
     II.a) Size: 20
     II.b) Type: DNA
     II.c) Organism: artificial sequence
      III) Characteristic:
    III.a) other relevant information: primer for SNP genotyping
           CATGATTCGCCAGTTCTTCA 20
      I.a) Sequence identifying number: SEQ ID No. 17
       II) Sequence features:
     II.a) Size: 20
     II.b) Type: DNA
     II.c) Organism: artificial sequence
      III) Characteristic:
    III.a) other relevant information: primer for SNP genotyping
           CATGGTTCCACCAGTCCATT 20
      I.a) Sequence identifying number: SEQ ID No. 18
       II) Sequence features:
     II.a) Size: 20
     II.b) Type: DNA
     II.c) Organism: artificial sequence
      III) Characteristic:
    III.a) other relevant information: primer for SNP genotyping
           CGATTGAAGCCACTGAACAA 20
      I.a) Sequence identifying number: SEQ ID No. 19
       II) Sequence features:
     II.a) Size: 22
     II.b) Type: DNA
     II.c) Organism: artificial sequence
      III) Characteristic:
    III.a) other relevant information: primer for SNP genotyping
           TCAGCTGGAATGTTGAAGAGAA                                     22
```

SEQUENCE LISTING

```
    I.a) Sequence identifying number: SEQ ID No. 20
     II) Sequence features:
   II.a) Size: 20
   II.b) Type: DNA
   II.c) Organism: artificial sequence
    III) Characteristic:
  III.a) other relevant information: primer for SNP genotyping
        TAACAGCAGCCCCTTTCAGT 20
    I.a) Sequence identifying number: SEQ ID No. 21
     II) Sequence features:
   II.a) Size: 20
   II.b) Type: DNA
   II.c) Organism: artificial sequence
    III) Characteristic:
  III.a) other relevant information: primer for SNP genotyping
        TGAAAGGGGCTGCTGTTAAT 20
    I.a) Sequence identifying number: SEQ ID No. 22
     II) Sequence features:
   II.a) Size: 20
   II.b) Type: DNA
   II.c) Organism: artificial sequence
    III) Characteristic:
  III.a) other relevant information: primer for SNP genotyping
        TGGCCATGCTCACTTGTTTA 20
    I.a) Sequence identifying number: SEQ ID No. 23
     II) Sequence features:
   II.a) Size: 20
   II.b) Type: DNA
   II.c) Organism: artificial sequence
    III) Characteristic:
  III.a) other relevant information: primer for SNP genotyping
        TCGTCTTCCCTGCCTCTAAG 20
    I.a) Sequence identifying number: SEQ ID No. 24
     II) Sequence features:
   II.a) Size: 20
   II.b) Type: DNA
   II.c) Organism: artificial sequence
    III) Characteristic:
  III.a) other relevant information: primer for SNP genotyping
        GAATGGGCATGTCTCAGTTG 20
    I.a) Sequence identifying number: SEQ ID No. 25
     II) Sequence features:
   II.a) Size: 20
   II.b) Type: DNA
   II.c) Organism: artificial sequence
    III) Characteristic:
  III.a) other relevant information: primer for SNP genotyping
        ATGCCCATTCCGTTGTACTC 20
    I.a) Sequence identifying number: SEQ ID No. 26
     II) Sequence features:
   II.a) Size: 20
   II.b) Type: DNA
   II.c) Organism: artificial sequence
    III) Characteristic:
  III.a) other relevant information: primer for SNP genotyping
        GTGCTGGCCTGAATTTCTTT 20
    I.a) Sequence identifying number: SEQ ID No. 27
     II) Sequence features:
   II.a) Size: 21
   II.b) Type: DNA
   II.c) Organism: artificial sequence
```

SEQUENCE LISTING

```
        III) Characteristic:
     III.a) other relevant information: primer for SNP genotyping
           CCGTGATGTTTGCTCTCAGAT
21
       I.a) Sequence identifying number: SEQ ID No. 28
        II) Sequence features:
      II.a) Size: 20
      II.b) Type: DNA
      II.c) Organism: artificial sequence
       III) Characteristic:
     III.a) other relevant information: primer for SNP genotyping
           GGGCCAGTGTTGAATGAGTT
20
       I.a) Sequence identifying number: SEQ ID No. 29
        II) Sequence features:
      II.a) Size: 20
      II.b) Type: DNA
      II.c) Organism: artificial sequence
       III) Characteristic:
     III.a) other relevant information: primer for SNP genotyping
           GGTCATCGTGTCCTCCTTTC
20
       I.a) Sequence identifying number: SEQ ID No. 30
        II) Sequence features:
      II.a) Size: 20
      II.b) Type: DNA
      II.c) Organism: artificial sequence
       III) Characteristic:
     III.a) other relevant information: primer for SNP genotyping
           GGGCCAGTGTTGAATGAGTT
20
       I.a) Sequence identifying number: SEQ ID No. 31
        II) Sequence features:
      II.a) Size: 20
      II.b) Type: DNA
      II.c) Organism: artificial sequence
       III) Characteristic:
     III.a) other relevant information: primer for SNP genotyping
           ATCAGTTCTGCCCACCGTTT
20
       I.a) Sequence identifying number: SEQ ID No. 32
        II) Sequence features:
      II.a) Size: 22
      II.b) Type: DNA
      II.c) Organism: artificial sequence
       III) Characteristic:
     III.a) other relevant information: primer for SNP genotyping
           GATGGTCTTGATGGTCTGATGA
22
```

The invention claimed is:

1. An isolated nucleic acid molecule, wherein the nucleic acid molecule comprises a nucleic acid sequence selected from the group consisting of SEQ ID NOs: 1 and 2.

2. A kit for the early identification of fat deposition in bovines, wherein said kit comprises:
   (i) primers for amplifying a portion of a DDEF1 gene sequence, comprising a first primer molecule comprising the nucleotide sequence of SEQ ID NO: 1, a second primer molecule comprising the nucleotide sequence of SEQ ID NO: 2, a third primer molecule comprising the nucleotide sequence of SEQ ID NO: 3, and a fourth primer molecule comprising the nucleotide sequence of SEQ ID NO: 4;
   (ii) reagents for use in a genotyping reaction; and
   (iii) a manual containing instructions for identifying and interpreting results obtained with said genotyping reaction.

3. The kit of claim 2, wherein said kit further comprises a reagent selected from the group consisting of Tris-HCl, KCl, DMSO, $MgCl_2$, dNTP and Taq DNA polymerase.

* * * * *

SEQUENCE LISTING

<160> NUMBER OF SEQ ID NOS: 32

<210> SEQ ID NO 1
<211> LENGTH: 29
<212> TYPE: DNA
<213> ORGANISM: Artificial Sequence
<220> FEATURE:
<223> OTHER INFORMATION: Synthetic polynucleotide

<400> SEQUENCE: 1
atatgggaat cctagagagg agacgtaac                                    29

<210> SEQ ID NO 2
<211> LENGTH: 25

<212> TYPE: DNA
<213> ORGANISM: Artificial Sequence
<220> FEATURE:
<223> OTHER INFORMATION: Synthetic polynucleotide

<400> SEQUENCE: 2
gggaatccta gagaggagac gtaat                                              25

<210> SEQ ID NO 3
<211> LENGTH: 24
<212> TYPE: DNA
<213> ORGANISM: Artificial Sequence
<220> FEATURE:
<223> OTHER INFORMATION: Synthetic polynucleotide

<400> SEQUENCE: 3
gactagaaat aggagacccg gacc                                               24

<210> SEQ ID NO 4
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 4
gccttcctca aaccacacat                                                    20

<210> SEQ ID NO 5
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 5
attgctcacc tgcccagttt                                                    20

<210> SEQ ID NO 6
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 6
gccttcctca aaccacacat                                                    20

<210> SEQ ID NO 7
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 7
taataaacgg cagcccagac                                                    20

<210> SEQ ID NO 8
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 8
ccccacatgt taaacacacg                                              20

<210> SEQ ID NO 9
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 9
cgcacagtta aaagccattg                                              20

<210> SEQ ID NO 10
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 10
ccagcataca cctcctctca                                              20

<210> SEQ ID NO 11
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 11
gctgaaacaa aaaggtgcaa                                              20

<210> SEQ ID NO 12
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 12
acagctaagc aggggaaacc                                              20

<210> SEQ ID NO 13
<211> LENGTH: 21
<212> TYPE: DNA
<213> ORGANISM: Artificial Sequence
<220> FEATURE:
<223> OTHER INFORMATION: Synthetic polynucleotide

<400> SEQUENCE: 13
ttccctcctg ttactgcttg a                                            21

<210> SEQ ID NO 14
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 14
ctccacgtcc ataatgctga                                              20

<210> SEQ ID NO 15

```
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 15
gggtgtttca taggcctcac                                                    20

<210> SEQ ID NO 16
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 16
catgattcgc cagttcttca                                                    20

<210> SEQ ID NO 17
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 17
catggttcca ccagtccatt                                                    20

<210> SEQ ID NO 18
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 18
cgattgaagc cactgaacaa                                                    20

<210> SEQ ID NO 19
<211> LENGTH: 22
<212> TYPE: DNA
<213> ORGANISM: Artificial Sequence
<220> FEATURE:
<223> OTHER INFORMATION: Synthetic polynucleotide

<400> SEQUENCE: 19
tcagctggaa tgttgaagag aa                                                 22

<210> SEQ ID NO 20
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 20
taacagcagc ccctttcagt                                                    20

<210> SEQ ID NO 21
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 21
```

-continued tgaaaggggc tgctgttaat                                              20

<210> SEQ ID NO 22
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 22
tggccatgct cacttgttta                                              20

<210> SEQ ID NO 23
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 23
tcgtcttccc tgcctctaag                                              20

<210> SEQ ID NO 24
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 24
gaatgggcat gtctcagttg                                              20

<210> SEQ ID NO 25
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 25
atgcccattc cgttgtactc                                              20

<210> SEQ ID NO 26
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 26
gtgctggcct gaatttcttt                                              20

<210> SEQ ID NO 27
<211> LENGTH: 21
<212> TYPE: DNA
<213> ORGANISM: Artificial Sequence
<220> FEATURE:
<223> OTHER INFORMATION: Synthetic polynucleotide

<400> SEQUENCE: 27
ccgtgatgtt tgctctcaga t                                            21

<210> SEQ ID NO 28
<211> LENGTH: 20
<212> TYPE: DNA

```
<213> ORGANISM: Artificial Sequence
<220> FEATURE:
<223> OTHER INFORMATION: Synthetic polynucleotide

<400> SEQUENCE: 28
gggccagtgt tgaatgagtt                                                    20

<210> SEQ ID NO 29
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 29
ggtcatcgtg tcctcctttc                                                    20

<210> SEQ ID NO 30
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 30
gggccagtgt tgaatgagtt                                                    20

<210> SEQ ID NO 31
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 31
atcagttctg cccaccgttt                                                    20

<210> SEQ ID NO 32
<211> LENGTH: 22
<212> TYPE: DNA
<213> ORGANISM: Artificial Sequence
<220> FEATURE:
<223> OTHER INFORMATION: Synthetic polynucleotide

<400> SEQUENCE: 32
gatggtcttg atggtctgat ga                                                 22
```